(12) United States Patent
Onis et al.

(10) Patent No.: US 10,206,945 B2
(45) Date of Patent: Feb. 19, 2019

(54) BIOACTIVE COATINGS

(71) Applicant: BioInteractions Ltd., Reading, Berkshire (GB)

(72) Inventors: Simon Onis, Reading (GB); Fanny Burrows, Reading (GB); Krishan Kapoor, Epsom Downs (GB); Alan Rhodes, Winnersh (GB); Ajay Luthra, Ruislip (GB)

(73) Assignee: BioInteractions Ltd., Reading, Berkshire (GB)

( * ) Notice: Subject to any disclaimer, the term of this patent is extended or adjusted under 35 U.S.C. 154(b) by 0 days.

(21) Appl. No.: 14/263,387

(22) Filed: Apr. 28, 2014

(65) Prior Publication Data

US 2014/0322287 A1    Oct. 30, 2014

Related U.S. Application Data

(60) Provisional application No. 61/816,519, filed on Apr. 26, 2013.

(51) Int. Cl.

| | |
|---|---|
| *A61K 31/728* | (2006.01) |
| *A61K 47/32* | (2006.01) |
| *A61K 31/131* | (2006.01) |
| *A61K 9/00* | (2006.01) |
| *A61K 31/727* | (2006.01) |
| *A61K 31/14* | (2006.01) |
| *A61L 27/16* | (2006.01) |
| *A61L 27/26* | (2006.01) |
| *A61L 27/34* | (2006.01) |
| *A61L 27/54* | (2006.01) |
| *A61L 29/04* | (2006.01) |
| *A61L 29/08* | (2006.01) |
| *A61L 29/16* | (2006.01) |
| *A61L 31/04* | (2006.01) |
| *A61L 31/10* | (2006.01) |
| *A61L 31/16* | (2006.01) |
| *A61L 33/00* | (2006.01) |
| *A61L 33/06* | (2006.01) |

(52) U.S. Cl.
CPC .......... *A61K 31/728* (2013.01); *A61K 9/0012* (2013.01); *A61K 31/131* (2013.01); *A61K 31/14* (2013.01); *A61K 31/727* (2013.01); *A61K 47/32* (2013.01); *A61L 27/16* (2013.01); *A61L 27/26* (2013.01); *A61L 27/34* (2013.01); *A61L 27/54* (2013.01); *A61L 29/041* (2013.01); *A61L 29/049* (2013.01); *A61L 29/085* (2013.01); *A61L 29/16* (2013.01); *A61L 31/041* (2013.01); *A61L 31/048* (2013.01); *A61L 31/10* (2013.01); *A61L 31/16* (2013.01); *A61L 33/0011* (2013.01); *A61L 33/064* (2013.01); *A61L 2300/206* (2013.01); *A61L 2300/208* (2013.01); *A61L 2300/236* (2013.01); *A61L 2300/404* (2013.01); *A61L 2300/42* (2013.01); *A61L 2300/44* (2013.01); *A61L 2300/45* (2013.01)

(58) Field of Classification Search
CPC .... A61K 31/728; A61K 9/0012; A61K 47/32; A61K 31/131; A61K 31/14; A61K 31/727; A61L 31/041; A61L 31/048; A61L 31/10; A61L 31/16; A61L 29/041; A61L 33/0011; A61L 33/064; A61L 27/16; A61L 27/26; A61L 27/34; A61L 27/54; A61L 29/049; A61L 29/085; A61L 29/16

See application file for complete search history.

(56) References Cited

U.S. PATENT DOCUMENTS

| | | |
|---|---|---|
| 3,730,701 A | 5/1973 | Isquith et al. |
| 3,794,736 A | 2/1974 | Abbott et al. |
| 3,860,709 A | 1/1975 | Abbott et al. |
| 4,082,727 A | 4/1978 | Nagata et al. |
| 4,239,664 A | 12/1980 | Teng et al. |
| 4,282,366 A | 8/1981 | Eudy |
| 4,331,697 A | 5/1982 | Kudo et al. |
| 4,394,378 A | 7/1983 | Klein |
| 4,408,996 A | 10/1983 | Baldwin |
| 4,414,268 A | 11/1983 | Baldwin |
| 4,504,541 A | 3/1985 | Yasuda et al. |
| 4,615,937 A | 10/1986 | Bouchette |

(Continued)

FOREIGN PATENT DOCUMENTS

| | | |
|---|---|---|
| EP | 0456093 | 11/1991 |
| EP | 0596615 | * 5/1994 |

(Continued)

OTHER PUBLICATIONS

International Search Report and Written Opinion from corresponding PCT Application No. PCT/GB2014/000164, 9 pages, dated Sep. 19, 2014.

*Primary Examiner* — Johann R Richter
*Assistant Examiner* — Genevieve S Alley
(74) *Attorney, Agent, or Firm* — Christensen, Fonder, Dardi & Herbert PLLC; Curtis Herbert

(57) ABSTRACT

Antimicrobial and antithrombogenic polymer or polymeric blend, compounds, coatings, and materials containing the same, as well as articles made with, or coated with the same, and methods of making the same exhibiting improved antimicrobial properties and reduced platelet adhesion. Embodiments include polymers with antimicrobial and antithrombogenic groups bound to a single polymer backbone, an antimicrobial polymer blended with an antithrombogenic polymer, and medical devices coated with the antimicrobial and antithrombogenic polymer or polymeric blend.

27 Claims, 7 Drawing Sheets

(56) References Cited

U.S. PATENT DOCUMENTS

| | | |
|---|---|---|
| 4,620,878 A | 11/1986 | Gee |
| 4,631,273 A | 12/1986 | Blehm et al. |
| 4,670,592 A | 6/1987 | Eakin et al. |
| 4,748,189 A * | 5/1988 | Su et al. ............... 514/781 |
| 4,987,181 A | 1/1991 | Bichon et al. |
| 5,183,872 A | 2/1993 | Heidel et al. |
| 5,344,455 A | 9/1994 | Keogh et al. |
| 5,358,688 A | 10/1994 | Robertson |
| 5,359,104 A | 10/1994 | Higgs et al. |
| 5,462,976 A | 10/1995 | Matsuda et al. |
| 5,512,329 A | 4/1996 | Guire et al. |
| 5,583,213 A | 12/1996 | Yafuso et al. |
| 5,728,751 A | 3/1998 | Patnaik |
| 5,741,551 A | 4/1998 | Guire et al. |
| 5,741,881 A | 4/1998 | Patnaik |
| 5,763,504 A | 6/1998 | Matsuda et al. |
| 5,776,184 A | 7/1998 | Tuch |
| 5,783,570 A | 7/1998 | Yokota et al. |
| 5,837,747 A | 11/1998 | Soon Shiong et al. |
| 5,846,530 A | 12/1998 | Soon Shiong et al. |
| 5,855,618 A | 1/1999 | Patnaik et al. |
| 5,877,263 A | 3/1999 | Patnaik et al. |
| 5,945,457 A | 8/1999 | Plate et al. |
| 5,993,890 A | 11/1999 | Marchant et al. |
| 6,060,582 A | 5/2000 | Hubbell et al. |
| 6,096,798 A | 8/2000 | Luthra et al. |
| 6,107,416 A | 8/2000 | Patnaik et al. |
| 6,121,027 A | 9/2000 | Clapper et al. |
| 6,127,348 A | 10/2000 | Roufa et al. |
| 6,287,707 B1 | 9/2001 | Luthra et al. |
| 6,440,571 B1 * | 8/2002 | Valint, Jr. ............... A61L 27/34 351/159.33 |
| 7,256,218 B2 | 8/2007 | Jacbus et al. |
| 7,563,792 B2 | 7/2009 | Jacbus et al. |
| 7,771,743 B1 | 8/2010 | Luthra et al. |
| 8,101,196 B2 | 1/2012 | Luthra et al. |
| 8,512,731 B2 | 8/2013 | Yang et al. |
| 8,541,498 B2 | 9/2013 | Sandhu et al. |
| 8,598,269 B2 | 12/2013 | Neff et al. |
| 8,603,453 B2 | 12/2013 | Hodge et al. |
| 2003/0021762 A1 | 1/2003 | Luthra et al. |
| 2003/0203991 A1 * | 10/2003 | Schottman et al. ......... 523/334 |
| 2004/0170752 A1 * | 9/2004 | Luthra et al. ............... 427/2.24 |
| 2005/0256509 A1 * | 11/2005 | Sakai ............... A61M 25/0068 604/537 |
| 2006/0134166 A1 | 6/2006 | Luthra et al. |
| 2006/0223962 A1 | 10/2006 | Getman et al. |
| 2008/0032889 A1 | 2/2008 | Blettner et al. |
| 2009/0306157 A1 | 12/2009 | Rohrer et al. |
| 2011/0124772 A1 * | 5/2011 | Wang ............... A01N 33/12 523/177 |
| 2011/0274821 A1 | 11/2011 | Luthra et al. |
| 2012/0184940 A1 * | 7/2012 | Ying et al. ............... 604/508 |
| 2013/0053470 A1 | 2/2013 | Raisin-Dadre et al. |

FOREIGN PATENT DOCUMENTS

| | | |
|---|---|---|
| EP | 1175148 * | 1/2002 |
| EP | 1624754 | 2/2011 |
| GB | 705838 | 3/1954 |
| GB | 1095902 | 12/1967 |
| WO | 9741164 | 11/1997 |
| WO | 9916475 | 4/1999 |
| WO | 0065915 | 11/2000 |
| WO | 2013152838 | 10/2013 |

* cited by examiner

Light Microscopy of Platelet Adhesion (after exposure to 1x10⁵ platelets/ul PRP):

Uncoated Polyurethane         90% PHMB-                    75% PHMB-
                              polymer:10% heparin          polymer:25%
                              polymer                      heparin- polymer Light Microscopy of Platelet Adhesion (after exposure to $1 \times 10^5$ platelets/ul PRP)

Uncoated          Combination Polymer 33      Combination Polymer 46

Polyurethane

Combination Polymer (High Heparin) from Example 12

BIOACTIVE COATINGS

CROSS-REFERENCE TO RELATED APPLICATIONS

This patent application claims priority to provisional patent application U.S. 61/816,519 filed Apr. 26, 2013, which is hereby incorporated by reference herein.

FIELD OF THE INVENTION

The Technical Field relates to anti-microbial and anti-thrombogenic polymers, compounds, coatings, and materials containing the same, as well as articles made with, or coated with the same, and methods of making the same.

BACKGROUND

In recent years, antimicrobial materials have been widely used as a coating for various surfaces, especially those used in medical applications. These coatings reduce the likelihood of complications based on infection. Anti-fouling materials have also been used to coat these surfaces and reduce the likelihood of device related complications.

SUMMARY OF THE INVENTION

Polymeric materials are described herein that can be coated onto various articles and can give enhanced antimicrobial properties and reduced platelet adhesion. These polymeric materials can be used to make or coat a range of medical devices. Embodiments include polymers comprising an antimicrobial and an antithrombogenic moiety bound to the same polymeric backbone or a polymeric blend comprising a polymer with an antimicrobial moiety and a polymer with an antithrombogenic moiety. Polymers and polymeric blends described herein have been found to have surprisingly superior antimicrobial activity over polymers currently in use, especially with regard to gram negative bacteria (e.g. *Pseudomonas aeruginosa*).

A compound comprising a polymer, an antithrombogenic agent, and an antimicrobial agent, with the antithrombogenic agent and the antimicrobial agent are covalently bound to the polymer. The antimicrobial agent may comprise a guanidine group or a quaternary ammonium salt. The polymer may comprise polymerized vinylic, allylic groups, methacrylate groups, acrylate groups, or combinations thereof. The antithrombogenic agent may comprise a polysaccharide, a glycosaminoglycan, warfarin, hirudin, heparin group, or combinations thereof. The polymer may further comprise a lubricant group and/or an anti-fouling group covalently bound to or blended with the polymer.

A second embodiment is a polymeric coating comprising the polymer described above.

Another embodiment is a medical device comprising a coating of the same.

A further embodiment is a method for making a polymer comprising polymerizing a mixture of an antimicrobial agent and an antithrombogenic agent at a desired ratio. The antimicrobial agent comprises a first backbone precursor with a covalently bound antimicrobial compound, a first polymerizable group, and the antithrombogenic agent comprises a second backbone precursor with a covalently bound antithrombogenic compound and a second polymerizable group.

An additional embodiment is a polymer blend comprising an antimicrobial polymer blended with an antithrombogenic polymer with the antimicrobial polymer comprising a first backbone, a first attachment group covalently bound to the first backbone, and an antimicrobial group covalently bound to the first attachment group. The antithrombogenic polymer comprises a second backbone, a second attachment group covalently bound to the second backbone, and an antithrombogenic group covalently bound to the second attachment group.

The term "agent" as used in the claims and description herein, in the expressions "antithrombogenic agent", "antimicrobial agent" "therapeutic agent and the like, extends not only to compounds as such, including but not limited to monomers and polymers, but also to correspondingly active parts of compounds, such as radicals and groups, having the relevant property.

DETAILED DESCRIPTION

Figure 1:
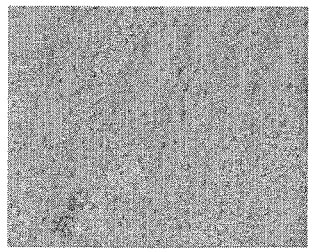
FIG. 1 is a series of light microscopy photos depicting platelet adhesion on uncoated polyurethane, polyurethane coated with 90% polyhexamethylene biguanide polymer: 10% heparin polymer, and polyurethane coated with 75% polyhexamethylene biguanide polymer: 25% heparin polymer.
Figure 1:
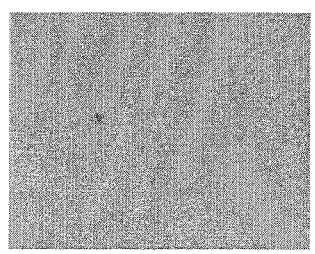
Figure 1:
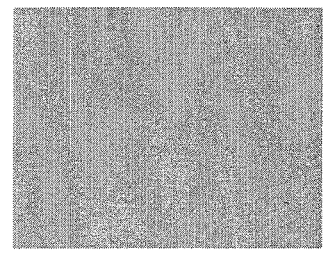

Polymeric materials are described herein that can be coated onto various articles and can give enhanced antimicrobial properties and improved blood compatibility. These polymeric materials can be used to make or coat a range of medical devices. Embodiments include polymers comprising an antimicrobial and an antithrombogenic moiety bound to and/or part of the same polymer backbone or a polymeric blend comprising a polymer with an antimicrobial moiety and a polymer with an antithrombogenic moiety. Polymers and polymeric blends described herein have been found to have surprisingly superior antimicrobial activity over polymers currently in use, especially with regard to gram negative bacteria (e.g. *Pseudomonas aeruginosa*).

Polymers are molecules built up by the repetition of smaller units that are sometimes called monomers. Polymers are typically made by special chemical schemes that make the monomers chemically react with each other to form molecular chains that can range in length from short to very long molecules. Polymers can be assembled into larger materials; for example, many polymers may be linked together to form a hydrogel. The polymers may be crosslinked or may be free of crosslinks. Crosslinks are covalent bonds that link one polymer chain to another.

The antithrombogenic and antimicrobial groups may be pendant groups, which are independently chosen and attached to the polymer backbone. Pendant groups are groups attached to the polymer backbone. They may be attached after the polymer backbone is formed, or they may be attached to the monomers prior to polymerization. The various pendant groups will be independently attached to the polymer backbone so that the polymer will comprise the polymer backbone and a plurality of the pendant groups. Further, other pendant groups may be attached to the polymer, or the polymer may be free of pendant groups besides the antithrombogenic and/or antimicrobial groups. Polymer compositions generally have a distribution of molecular weights that can generally be characterized by an average property. The polymer, or the polymer backbone, may range in weight from, for instance, a minimum of 100 Daltons, or a minimum of 1,000 Daltons, up to a maximum of, for instance, 1,000,000 Daltons or 10,000,000 Daltons. Thus exemplary molecular weight ranges for the polymer, or for the polymer backbone, of 100 to 10,000,000 Daltons, or of 1,000 to 1,000,000 Daltons, are possible. Highly crosslinked polymer may not be readily characterized by a molecular weight, but the polymer can then be characterized by the polymer chain within the polymer and a degree of crosslinking. The amount of the antithrombogenic or antimicrobial group, which may be a pendant group, may be freely varied, for instance, from about 0.1% to about 99% w/w of the total compound that comprises the pendant group. In further embodiments the concentration (i.e. weight proportion) of the antithrombogenic pendant group to the total weight of the polymer may be at least 1%, or at least 1.5%, and may be not more than 8%, or not more than 20%. Thus the concentration ranges for the antithrombogenic group include, for example, about 1% to about 20%, or from about 1.5% to about 8%. In further embodiments the concentration (i.e. the weight proportion) of the antimicrobial pendant group to the total weight of the polymer may be at least 2%, or at least 6%, and may be not more than 7%, or not more than 10%. Thus the concentrations ranges for the antimicrobial group include, for example, about 2% to about 10%, or from about 6% to about 7%. A person of ordinary skill in the art will recognize that additional ranges are contemplated and are within the present disclosure. Artisans will immediately appreciate that all values and ranges within the expressly stated limits are contemplated, e.g., about. To achieve these ranges, for instance, the monomer compound may be polymerized from a concentrated state, or mixed with various other monomers for polymerization. Or a polymer may be selected to serve as the polymer backbone and lightly or heavily decorated with antithrombogenic/antimicrobial pendant groups, as well as other pendant groups.

FIG. 1 shows a series of three light microscopy photographs (photomicrographs) each at a magnification of ×400 of the platelet adhesion of an uncoated polyurethane, a polyurethane coated with a polymer of 90% PHMB-polymer (where PHMB denotes polyhexamethylene biguanide) and 10% heparin polymer, and a polyurethane coated with a polymer of 75% PHMB-polymer and 25% heparin polymer after exposure to $1 \times 10^5$ platelets/µl platelet rich plasma (PRP). It is apparent that the combination coatings each reduce the platelet adhesion.

Figure 2:
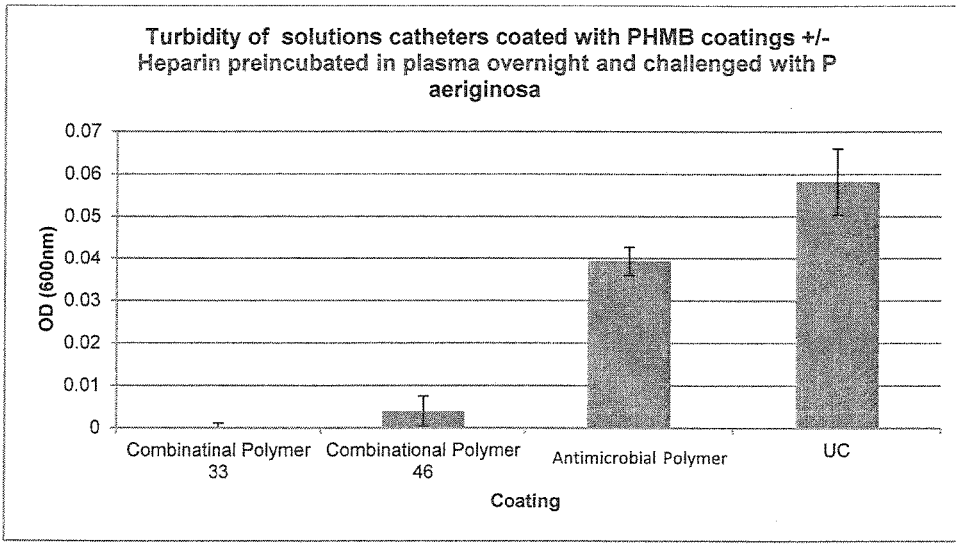
FIG. 2 is a graph of the turbidity of solutions associated with catheters comprising a combination polymer coating, an antimicrobial polymer coating, or no coating.

FIG. 2 is a graph of the turbidity of solutions associated with substrates coated with combination polymers, antimicrobial polymers, and uncoated. The substrate is treated with a bacterial source, given a proper amount of time for the bacteria to adhere to the surface, and then rinsed. The treated substrate is then placed in solution and the bacteria are allowed to proliferate. After a set period of time, the optical density (OD) of the solution is measured. Higher OD indicates that there are more bacteria present in the solution and therefore there were more bacteria present on the substrate. It can be seen in FIG. 2 that combination polymers provide significant improvements in antimicrobial proprieties with regard to *P. aeriginosa* over both uncoated substrates and substrates coated with an antimicrobial-only polymer.

Figure 3:
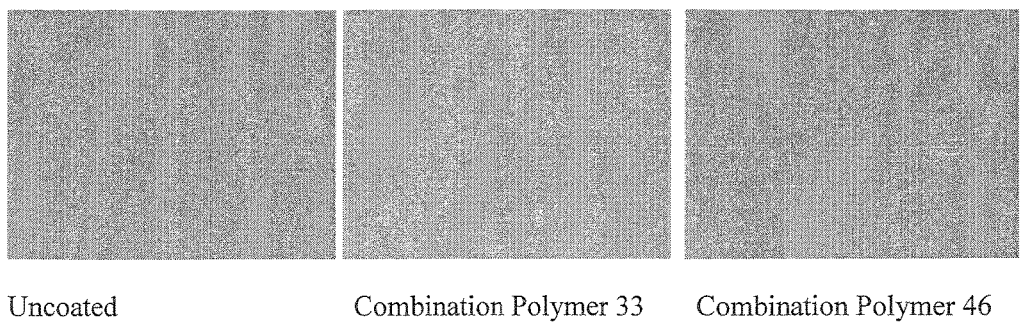
FIG. 3 is a series of light microscopy photos depicting platelet adhesion on uncoated polyurethane, and polyurethane coated with one of two polymers.

FIG. 3 is a series of three light microscopy photographs (photomicrographs ×400) of the platelet adhesion of an uncoated polyurethane, a polyurethane coated with the combination polymers tested in FIG. 2 after exposure to $1 \times 10^5$ platelets/µl PRP. The combination coatings are seen to reduce the platelet adhesion.

Example 1 describes the synthesis of an antithrombogenic monomer. Generally a monomer (e.g. poly(ethylene glycol) methacrylate) comprising a polymerizable group (e.g. methacrylate) with an attachment group (e.g. poly(ethylene glycol)) is activated and then mixed with the desired antithrombogenic group, typically in an active form, such as a salt. The monomer is then purified. A process similar to the one in Example 1 is used to create the antimicrobial monomer in Examples 4-6, 39, and 43.

Example 2 describes the process for complexing the antithrombogenic monomer if necessary to protect the functional group or make it easier to dissolve the monomer. The monomer/polymer can be decomplexed as described in Example 3.

Example 7 describes the process for synthesizing a combination polymer. In general the antithrombogenic monomer or the antimicrobial monomer is mixed with one or more co-monomers, degassed, and heated to the reaction temperature. The polymerization initiator is then added followed by the missing antithrombogenic monomer or antimicrobial monomer. The reaction is allowed to progress for a determined amount of time and then is quenched. The resulting polymer is then purified. A similar process to the one in Example 7 is used to create combination polymers in Examples 8-14, 40, and 44.

Example 15 describes the process for synthesizing an antimicrobial polymer. In general the antimicrobial monomer is mixed with one or more co-monomers, degassed, and heated to the reaction temperature. The polymerization initiator is then added. The reaction is allowed to progress to a desired viscosity and then is quenched. The resulting polymer is then purified. A similar process to the one in Example 15 is used to create antimicrobial polymers in Example 16. Example 17 describes the process for synthesizing an antithrombogenic polymer. In general the antithrombogenic monomer is mixed with one or more co-monomers, degassed, and heated to the reaction temperature. The polymerization initiator is then added. The reaction is allowed to progress to a desired viscosity and then is quenched. The resulting polymer is then purified. A similar process to the one in Example 17 is used to create antithrombogenic polymers in Examples 18-20.

Examples 21-27 describe possible process for coating a substrate with a polymeric coating using heat curing, UV curing, and dip coating.

Example 28 describes the method for testing the antimicrobial proprieties of coated substrates. Generally, test pieces are exposed to a particular medium (to enable protein adhesion etc.) such as plasma, blood or urine etc. for a predetermined time point, pieces are then washed then put into the test protocol. The test protocol effectively incubated the device with live microorganisms, washed device to removed "solution present bacteria", allowed the active component sufficient time to "kill", then transferred to growth media where viable microorganisms on the device will proliferate into daughter cells in solution hence increasing turbidity of growth media which can then be measured by optical density.

Example 29 describes the method for testing the platelet adhesion of a substrate. Generally, test pieces may (or may not be) exposed to a particular medium (to enable protein adhesion etc.) such as plasma, blood or urine etc. for a predetermined time point, pieces are then washed then put into the test protocol. The test protocol consists of exposing the treated pieces to plasma containing a certain concentration of platelets and allowed to sit overnight.

Example 30 describes the method for testing heparin activity.

Figure 4:
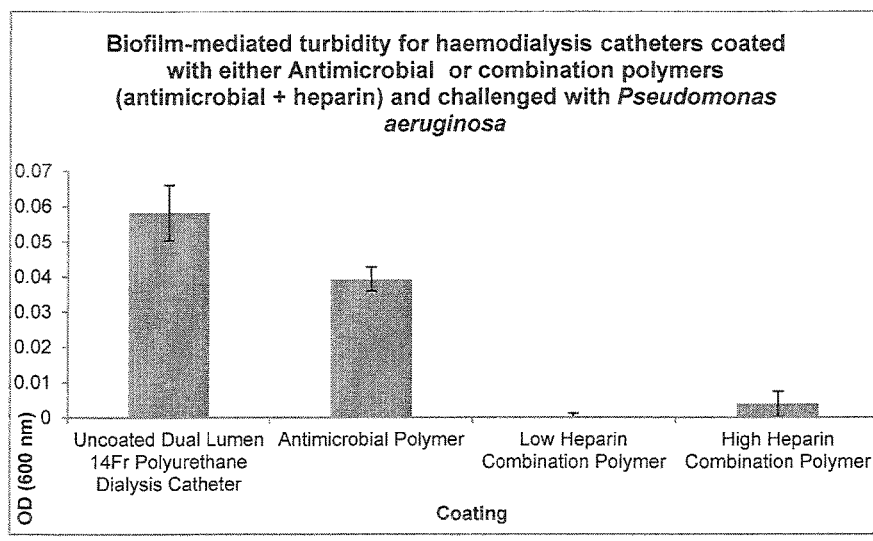
FIG. 4 is a graph of the turbidity of solutions associated with catheters comprising no coating, an antimicrobial polymer coating, or a combination coating comprising heparin when challenged with *Pseudomonas aeruginosa*.

Example 31 describes the general procedure for testing the activity of various coatings against *Pseudomonas aeruginosa*. The method is similar to the one described with regard to FIG. 2. FIG. 4 shows the results from Example 31, and it is clear from this graph that combination coatings show surprisingly superior antimicrobial activity relative to both the uncoated catheter and the antimicrobial polymer against *Pseudomonas aeruginosa*.

Figure 5:
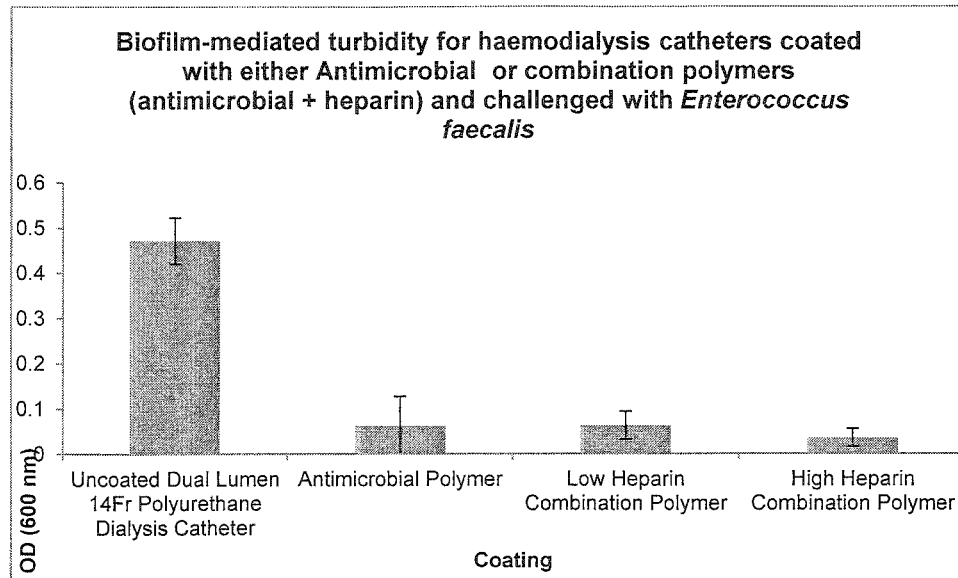
FIG. 5 is a graph of the turbidity of solutions associated with catheters comprising no coating, an antimicrobial polymer coating, or a combination coating comprising heparin when challenged with *Enterococcus faecalis*.
Figure 6:
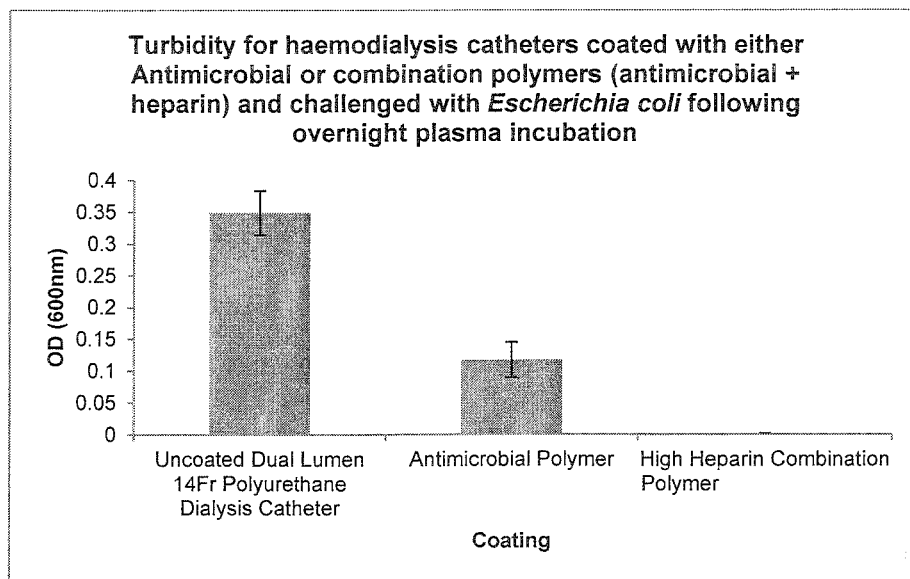
FIG. 6 is a graph of the turbidity of solutions associated with catheters comprising no coating, an antimicrobial polymer coating, or a combination coating comprising heparin when challenged with *Escherichia coli*.
Figure 7:
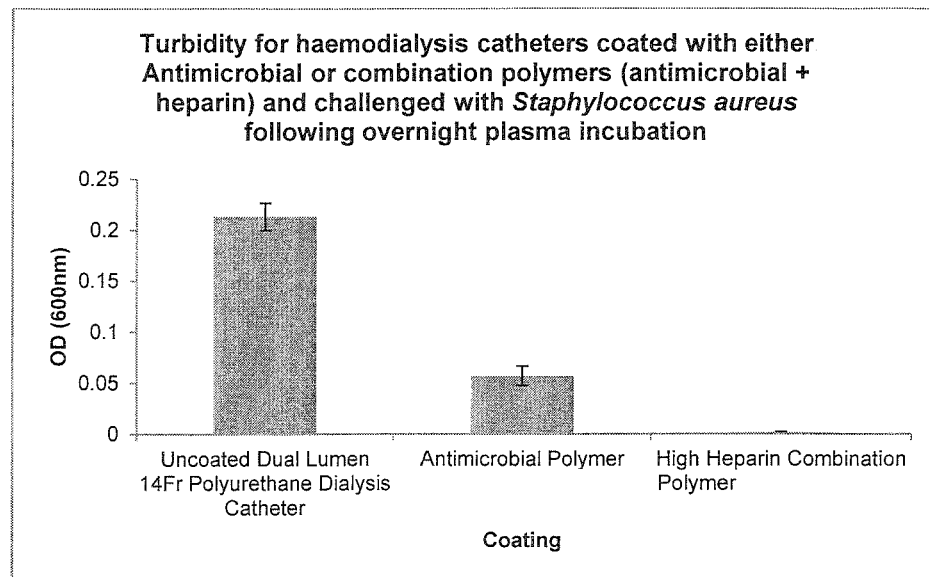
FIG. 7 is a graph of the turbidity of solutions associated with catheters comprising no coating, an antimicrobial polymer coating, or a combination coating comprising heparin when challenged with *Staphylococcus aureus*.
Figure 8:
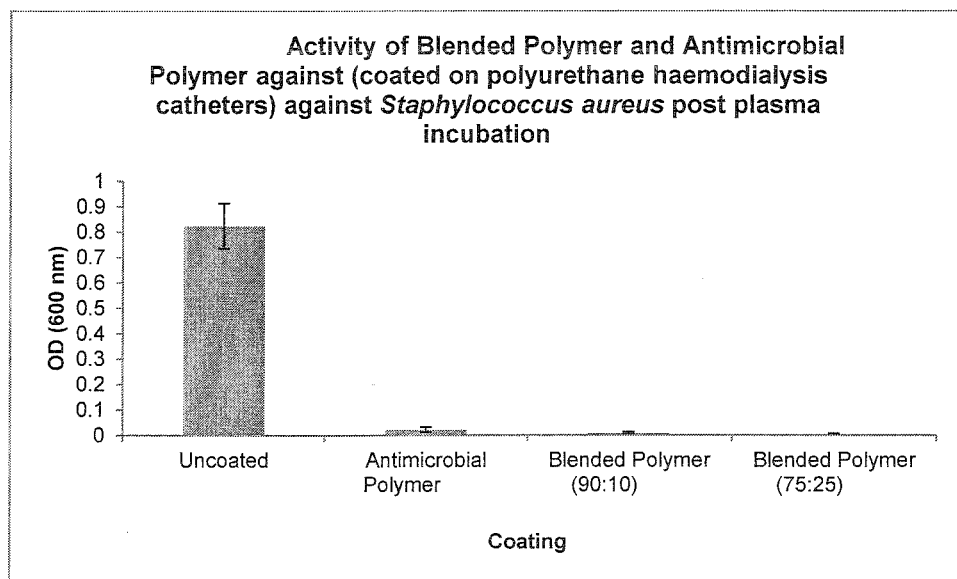
FIG. 8 is a graph of the turbidity of solutions associated with catheters comprising no coating, an antimicrobial polymer coating, or a combination coating comprising heparin when challenged with *Staphylococcus aures*.
Figure 9:
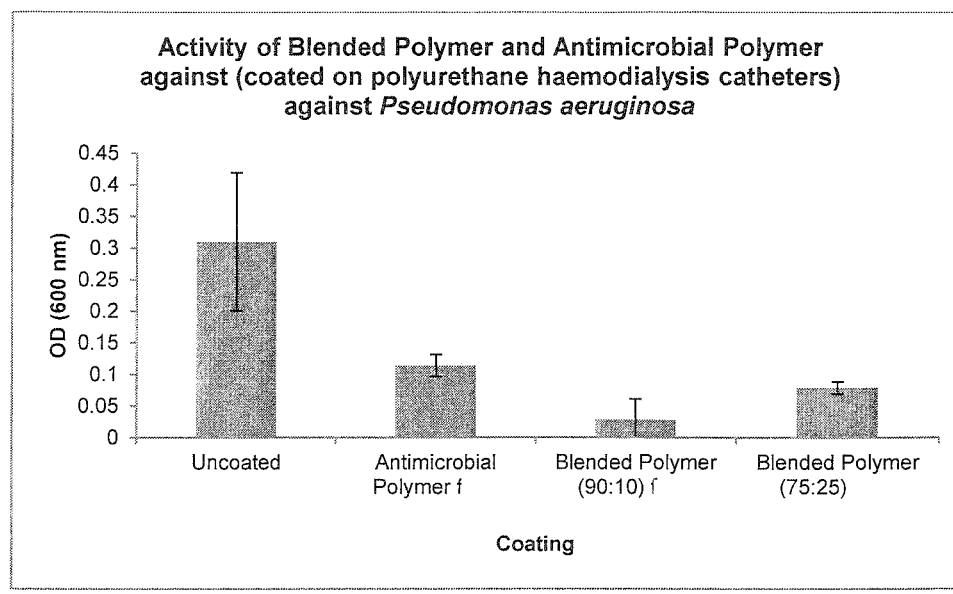
FIG. 9 is a graph of the turbidity of solutions associated with catheters comprising no coating, an antimicrobial polymer coating, or a combination coating comprising heparin when challenged with *Pseudomonas aeruginos*.

Examples 32-36 are conducted in a similar manner to Example 31. FIG. 5 shows the results from Example 32, and it is clear from this graph that combination coatings show superior antimicrobial activity relative to the uncoated catheter against *Enterococcus faecalis*. FIG. 6 shows the results from Example 33, and it is clear from this graph that combination coatings with a high heparin content show surprisingly superior antimicrobial activity relative to both the uncoated catheter and the antimicrobial polymer against *Escherichia coli*. FIG. 7 shows the results from Example 34, and it is clear from this graph that combination coatings with a high heparin content show surprisingly superior antimicrobial activity relative to both the uncoated catheter and the antimicrobial polymer against *staphylococcus aureus*. FIG. 8 shows the results from Example 35, and it is clear from this graph that combination coatings show superior antimicrobial activity relative to the uncoated catheter against *staphylococcus aureus*. FIG. 9 shows the results from Example 36, and it is clear from this graph that combination coatings show superior antimicrobial activity relative to the uncoated catheter against *Pseudomonas aeruginosa*.

Figure 10:
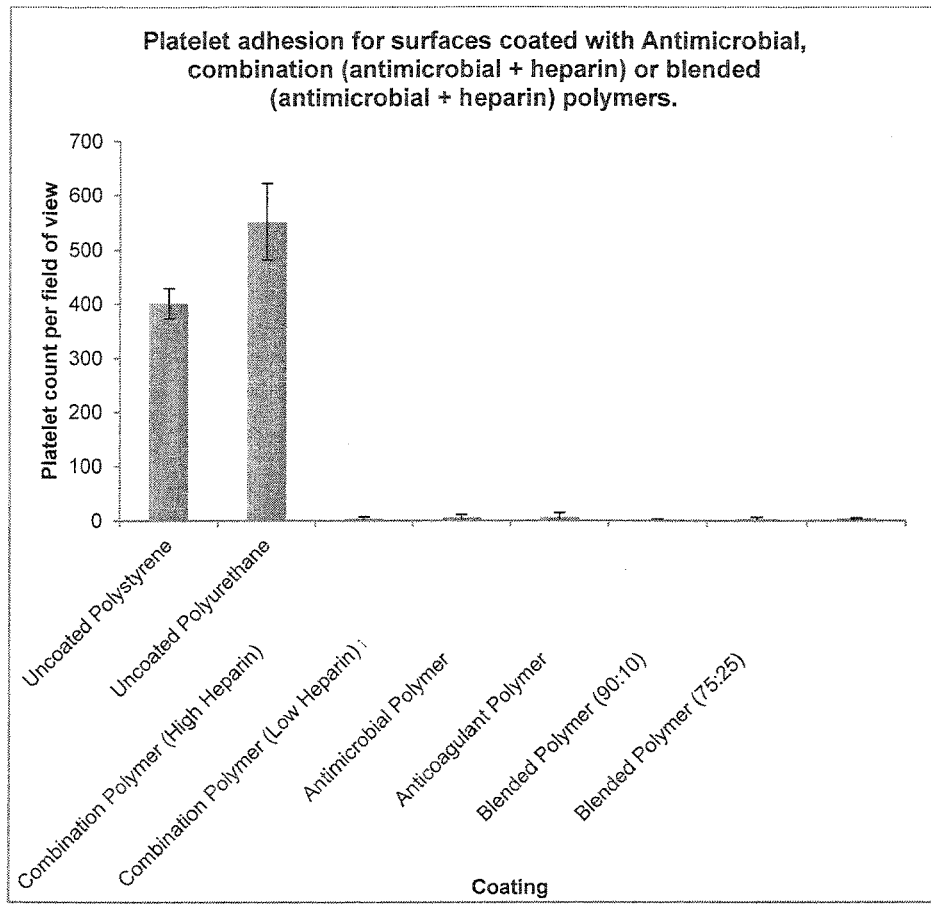
FIG. 10 is a graph of the platelet adhesion for surfaces coated with an antimicrobial polymer, a combination polymer, or a blended polymer.
Figure 11:
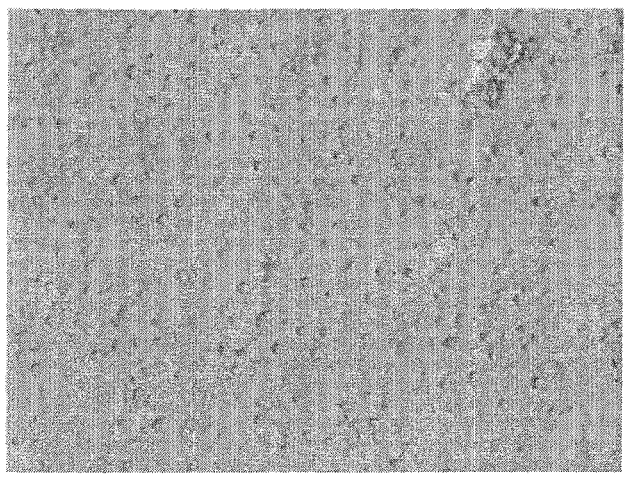
FIG. 11 is a light microscopy depicting the platelet adhesion for uncoated polyurethane.
Figure 12:
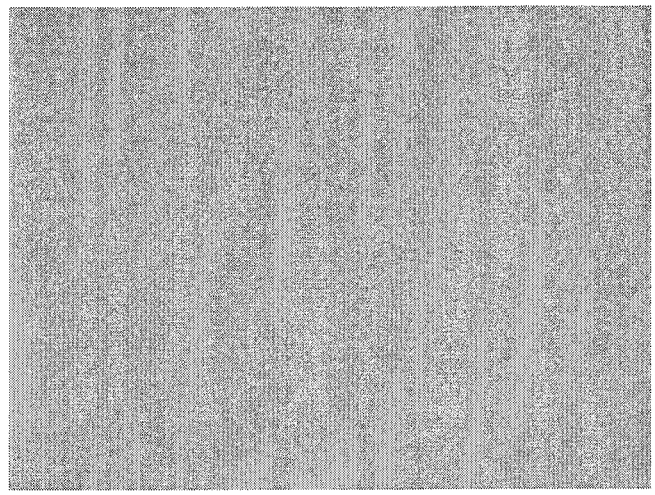
FIG. 12 is a light microscopy depicting the platelet adhesion for polyurethane coated with a combination polymer.

Example 37 tests the platelet adhesion as described above. The results are shown in FIGS. 10-12.

Figure 13:
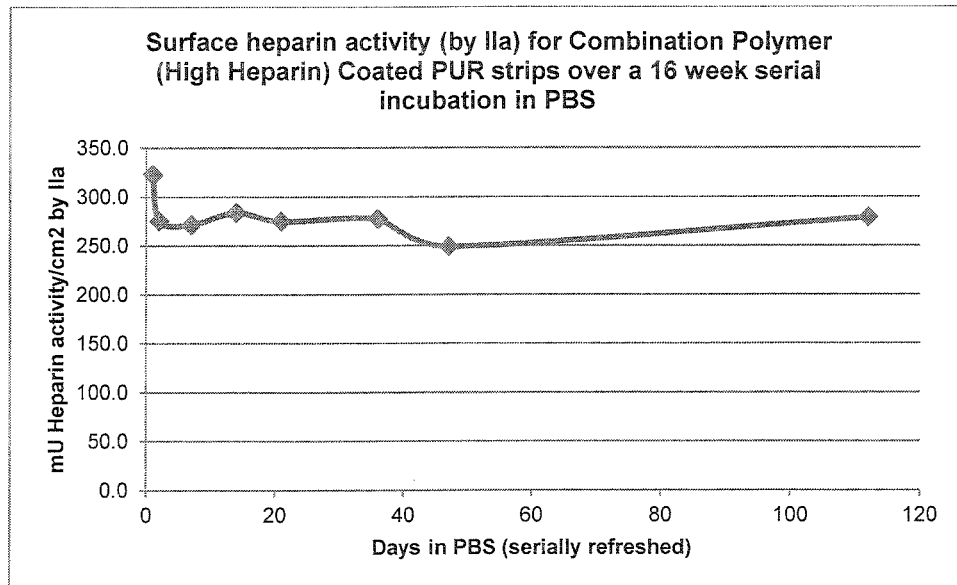
FIG. 13 is a graph of the surface heparin activity for a combination polymer over time.

Example 38 describes the heparin activity overtime for a combination polymer. The results are shown in FIG. 13.

Examples 41-42, 45, and 46 describe the process for polymerizing an antimicrobial monomer. In general the antimicrobial monomer is mixed with one or more co-monomers, degassed, and heated to the reaction temperature. The polymerization initiator is then added. The reaction is allowed to progress to a desired level of viscosity and then is quenched. The resulting polymer is then purified.

Antimicrobial functional groups are capable of killing, preventing the proliferation of, or inhibiting, or at least substantially slowing the growth of susceptible classes of microorganisms. Microorganisms include but are not necessarily limited to bacteria, viruses, fungi, yeasts, algae, and other life forms. Antimicrobial functional groups include guanide groups, biguanide groups, and quaternary amines.

Guanide groups have a portion of the compound with the general formula:

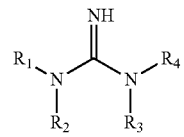

$R_1$, $R_2$, $R_3$, and $R_4$ are independently chosen from a group consisting of hydrogen, substituted or unsubstituted alkyl chains, substituted or unsubstituted cycloalkyls, substituted or unsubstituted aryls, substituted or unsubstituted alkoxys, amidines, and amines. Biguanide groups are a subgroup of guanide and have a portion of the compound with the general formula:

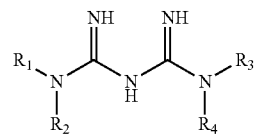

$R_1$, $R_2$, $R_3$, and $R_4$ are independently chosen from a group consisting of hydrogen, substituted or unsubstituted alkyl chains, substituted or unsubstituted cycloalkyls, substituted or unsubstituted aryls, substituted or unsubstituted alkoxys, amidines, and amines.

Suitable antimicrobial groups with biguanide and/or guanide groups include poly(guanides), poly(biguanides), poly(hexamethylene biguanide), chlorhexidine and their derivatives. Derivatives of the antimicrobial functional groups are also suitable for use as an antimicrobial functional group. Derivatives are compounds that can be derived from the parent compound by some chemical or physical process. Generally, they are similar in structure to the parent compound and possess similar characteristics. In some embodiments, the antimicrobial functional group may be a derivative of a groups containing a guanidine or biguanide group, for example poly(hexamethylene biguanide). Suitable derivatives of guanides, biguanides, and poly(hexamethylene biguanide) include those disclosed, for example, in U.S. Pat. Nos. 4,670,592; 8,603,453; 7,256,218; 7,563,792; U.S. 2009/0306157; WO 2013/152838; EP 1,624,754; EP 0,456,093; UK 705,838 and UK 1,095,902 which are hereby incorporated by reference herein in their entirety to the extent they do not contradict what is explicitly disclosed herein. These groups include guanide derivatives, polyaminopropyl biguanide derivative, polyhexamethylene guanididine and polyhexamethylene guanidine derivative and vinylic and methacrylated derivatives thereof.

Quaternary amine groups are cationic compounds comprising a group of the general formula:

$R_1$, $R_2$, $R_3$, $R_4$ may be independently selected from the group consisting of heteroatoms, substituted or unsubstituted alkyl chains, substituted or unsubstituted cycloalkyls, substituted or unsubstituted aryls, substituted or unsubstituted alkoxys, amidines, and amines. Suitable quaternary amine groups occur in organosilicon quaternary ammonium compounds and 3-(Trimethoxysilyl) propyldidecylmethyl ammonium salts as well as benzalkonium chloride, benzethonium chloride, methylbenzethonium chloride, cetalkonium chloride, cetylpridinium chloride, certimide, dofanium chloride, tetraethylammonium bromide, didecyldimethyl-ammonium chloride and domiphen bromide. Further suitable antimicrobial quaternary amine groups are disclosed in U.S. Pat. Nos. 8,598,269; 8,512,731; 3,794,736; 3,730,701; 3,860,709; 4,282,366; 4,394,378; 4,408,996; 4,414,268; 4,504,541; 4,615,937; 4,620,878; 4,631,273; 5,358,688; 5,359,104 and U.S. Publication No. 2006/0223962; which are hereby incorporated by reference herein in their entirety to the extent they do not contradict what is explicitly disclosed herein.

Antithrombogenic functional groups reduce the amount of thrombus formation in the body, generally following the introduction of a foreign object. Polysaccharides are polymers made from combinations of sugar monomer. Some polysaccharides have antithrombogenic properties including glycosaminoglycans, heparin, and their derivatives. Suitable antithrombogenic functional groups include heparin and heparin derivatives, glycosaminoglycans, warfarin, hirudin, hyaluronic acid, dermatan sulfate, polysaccharides, mucopolysaccharides, chondroitin sulfate, keratan sulfate, monomers having sulphate groups, sulphonate groups, sulphamate groups, polyoxyalkylene ether groups; zwitterionic groups, 2-sulphoethyl methacrylate, 2-sulphoethyl acrylate, 3-sulphopropyl methacrylate, 3-sulphopropyl ethoxy methacrylate, 3-sulphopropyl acrylate, 4-sulphatobutyl methacrylate, 4-sulphatobutyl acrylate, allyl sulphate, methyl ally sulphate, 3-buten-1-sulphate, -3-methyl-3-buten-1-sulphate, 3-methyl-3-buten-1-sulphate, 2-sulphatoethyl methacrylamide, 2-sulphatoethyl acrylamide, -3-sulphatopropyl methacrylamide, 3-sulphatopropyl acrylamide, 4-sulphatobutyl methacrylamide, 4-sulphatobutyl acrylamide, sulphato poly oxyalkylene methacrylate, sulphato polyoxyalkylene acrylate, 2-sulphamatoethyl methacrylate, 2-sulphamatoethyl acrylate, 3-sulphamatopropyl methacrylate, 3-sulphamatopropyl acrylate, 4-sulphamatobutyl methacrylate, 4-sulphamatobutyl acrylate, allyl sulphamate, methyl allyl sulphamate, 2-sulphamatoethyl methacrylamide, 2-sulphamatoethyl acrylamide, 3-sulphamatopropyl methacrylamide, 3-sulphamatopropylacrylamide, 4-sulphamatobutyl ethacrylamide, 4-sulphamatobutyl acrylamide, sulphamato polyoxyalkylene methacrylate, and sulphamato polyoxyalkylene acrylate. As can be seen from the foregoing named examples, the suitable monomers having sulphate, sulphonate and sulphamate groups, etc., can include polymerisable groups having carbon-carbon double bonds, especially acrylic and methacrylic groups. Further suitable antithrombogenic compounds and functional groups can be found in U.S. Publication No. 2011/0274821 and U.S. Pat. No. 6,096,798 which are hereby incorporated by reference herein in their entirety to the extent they do not contradict what is explicitly disclosed herein. Heparin groups are polysaccharides having a portion of the compound with the general formula:

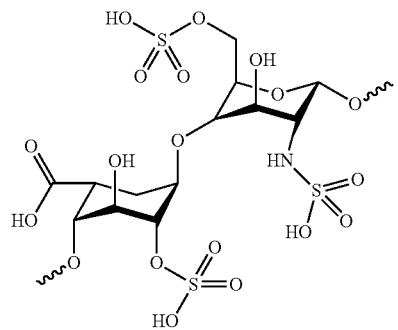

Derivatives of the antithrombogenic functional groups are also suitable for use as an antithrombogenic functional group. Derivatives are compounds that can be derived from the parent compound by some chemical or physical process. Generally, they are similar in structure to the parent compound and possess similar characteristics. In some embodiments, the antithrombogenic functional group may be a heparin derivative. Heparin derivatives, for example, include benzalkonium heparin, heparin sulfate, heparan sulfate, heparin ammonium, heparin benzyl ester, heparin calcium, heparin lithium, heparin sodium heparin salt, low and high molecular weight heparin, sulfated heparin, aminated heparin, heparin methacrylate, heparin quaternary ammonium salt complex methacrylate, heparin methacrylate salt, and heparin polyethylene glycol methacrylate.

A polymerizable group is a functional group that can be reacted to form a polymer. Polymerizable groups can be polymerizable by free-radical polymerization, addition polymerization, or condensation polymerization. Various monomers that contain polymerizable groups are disclosed in U.S. Pat. Nos. 6,127,348; 6,121,027; 7,771,743; PCT GB 9701173; U.S. Pat. Nos. 6,096,798; 6,060,582; 5,993,890; 5,945,457 ; 5,877,263; 5,855,618; 5,846,530; 5,837,747; 5,783,570; 5,776,184; 5,763,504; 5,741,881; 5,741,551; 5,728,751; 5,583,213; 5,512,329; 5,462,976; 5,344,455; 5,183,872; 4,987,181; 4,331,697; 4,239,664; 4,082,727; U.S. Publication No. 2003/0021762, and EP 049,828 A1 & B1. These references are hereby incorporated by reference herein to the extent it does not contradict what is explicitly disclosed herein for all purposes, including use of the monomers as co-monomers or making polymers for decoration with a functional compound. Further suitable polymerizable groups include poly(ethylene) oxide, polyethylene glycol, polyvinyl pyrrolidinone, polyacrylate, polymethylacrylate, polyalkylene oxide, methacrylic acid or other vinylic monomers, an acyl chloride, for example methacryloyl chloride, an isocyanate, or 2-isocyanatoethyl methacrylate an electrophilic poly(ethylene glycol) methacrylate (PEGMA). If PEGMA is used, PEGMA is made electrophilic by reacting it with epichlorohydrin first to attach an epoxide group onto PEGMA. The epoxide can then react with the amine on a functional group, or with other functional groups such as —OH, —COOH, etc. Additionally, PEGMA can be reacted with carbonyldiimidazole to give a reactive group that can further react with —NH, —OH, or —COOH.

Free radical polymerization is, in general, accomplished with a vinylic or allylic group, including acrylates and methacrylates. A monomer may be polymerized by itself or with co-monomers that also undergo free radical polymerization. Examples of co-monomers include one or more of: acrylates, methacrylates, 2-hydroxyethyl methacrylate, hydroxypropyl methacrylate, n-butyl methacrylate, tert-butyl methacrylate, n-hexyl methacrylate, 2-methoxyethyl methacrylate, poly(hexanide) methacrylate, poly(hexanide) polyethylene oxide methacrylate, or alkyl derivatized poly(hexanide) methacrylate, heparin derivatized polyethylene oxide macromer, vinyl sulfonic acid monomer, monomers comprising poly(ethylene glycol), N-vinyl pyrrolidone monomers, 4-benzoylphenyl methacrylate allyl methyl carbonate, allyl alcohol, allyl isocyanate, methacryloyloxyethyl phosphorylcholine, glycerol monomethacrylate, and biocompatible ampholyte monomers containing phosphate and amine moieties, such as those described in U.S. Publication No. 2013/0053470, which is hereby incorporated by reference herein in its entirety to the extent it does not contradict what is explicitly disclosed herein.

In some embodiments the antimicrobial and/or the antithormbogenic groups are covalently bound to their respective polymerizable groups through an attachment group. These attachment groups are generally a part of the backbone precursor and contain a reactive group that reacts with the desired amines or hydroxides to form the monomers that contain polymerizable groups. A variety of chemical options exist for making the linkage. For instance, the attachment group may be a substituted or unsubstituted hydrocarbon chain ranging from 1 to 13 carbons, a substituted or unsubstituted alkyl, a substituted or unsubstituted aryl, a substituted or unsubstituted cycloalkyl, a substituted or unsubstituted cycloalkenyl, a substituted or unsubstituted heterocycle, a substituted or unsubstituted alkenyl, a functional chain comprising an ester, a functional chain comprising an amide, a functional chain comprising a urea, a functional chain comprising a carbonate, a functional chain comprising a carbamate, a functional chain comprising a poly(ethylene oxide), and a functional chain comprising a poly(propylene) oxide polymer. The term substituted or unsubstituted is used to describe chemical functional group that may be itself substituted with one or more additional substitute groups. These additional substitute groups can include hetero atoms such as O, N, or S. However the number, substitution position and type of bonded substituent are not specifically limited unless specifically stated. Further suitable attachment groups include groups such as hydroxyl, carboxyl, anhydride, isocyanate, allyl, vinyl, acrylate, methacrylate, epoxide, sulfonic, or sulfate groups. Linkage to the polymer may be by covalent bonding (including grafting) or by ionic bonding. Chemical binding to a secondary amine nitrogen atom by means of isocyanate results in a substituted urea linkage, or by means of isothiocyanate results in a substituted thiourea linkage, or by means of expoxide results in a beta-hydroxyltertiary amine, or by means of acid chloride results in a N,N-disubstituted amide, or by means of acid anhydride results in a N,N-disubstituted amide, or by means of aldehyde or ketone results in N,N-disubstituted hemiaminals or aminals depending on the aldehyde or ketone, or by means of unsaturated bonds results in a tertiary amine linkage.

A polymer is a molecule composed of repeated subunits. The subunits are commonly referred as a monomeric unit or a mer. The term monomer is typically used to refer to a chemical subunit that is reactable to make a polymer. Polymers of only a few monomeric units are sometimes referred to as oligomers. The term polymer includes the meanings of homopolymer, copolymer, terpolymer, block copolymer, random copolymer, and oligomer. A polymer may include a block. A series of identical monomeric units joined together forms a block. A polymer may have no blocks, or a plurality of blocks. A copolymer is a polymer having at least two different monomeric units. Some copolymers have blocks, while others have random structures, and some copolymers have both blocks and regions of random copolymer bonding. Copolymers may be made from reactive monomers, oligomers, polymers, or other copolymers.

Free radical polymerization techniques are powerful tools for making polymers. In this technique, monomers in a solution are activated to form free radicals. A monomer with a free radical reacts with another monomer, forming a covalent bond, and that other monomer is activated to form a free radical. The resultant chain reaction is used to form polymers. There are other ways to form polymers, as well as techniques to include polymers or oligomers in the process of making a new polymer. These are well known to artisans and there are many such processes in common use. A process for making a copolymer is to join two other polymers together (precursor polymers, or precursors, in this context), typically by using functional groups on the two precursors that can react with each other to form a covalent bond. One of each of the two precursor polymers might be joined end to end to make a copolymer, or the precursors might be reacted to make polymers that have many of the precursors joined together. Two or more polymer precursors can be used. The processes detailed herein for making polymers can also be used to make copolymers. Moreover, polymers as described herein can have additional chemical groups, e.g., polymers, in their backbone. In polymer science, the backbone chain or main chain of a polymer is the series of covalently bonded atoms that together create the continuous chain of the molecule.

Accordingly, embodiments include polymers with antimicrobial groups and antithrombogenic groups that are copolymers. The copolymers may comprise one or more of various polymers. Various polymers include, for instance: hydrophilic polymers, hydrophobic polymers, polyalkylene oxides, polyethylene oxide, polyethers, and polyvinylpyrrolidone. As is evident, various polymers include, for example, polymers made with the polymerizable groups that are set forth herein, and which are not restated here for the sake of brevity.

The polymer may be crosslinked or may be free of crosslinks. Crosslinks are covalent bonds that link one polymer chain to another. Embodiments include polymers (a term including copolymers) that are crosslinked with a polyfunctional crosslinker. A polyfunctional crosslinker, as that term is used herein, is a molecule that comprises a two or more reactive groups that will form a covalent bond with the polymer. Some embodiments include polyfunctional crosslinkers having between 2 and 100 reactive groups; artisans will immediately appreciate that all ranges and values between the explicitly stated ranges are contemplated, for instance, lower limits of 3 or 5, or upper limits of 50 or 95, so suitable ranges may be between 3 and about 50 or from 5 to about 95. Examples include vinyls, epoxides, aldehydes, imines, isocyanates, benzophenones, aziridines, maleimides, diimides, carbodiimides, and succinimides. Further suitable crosslinkers include vinyl sulfonic acid, glycidyl methacrylate and other epoxide functional groups, alcohol methacrylate (HEMA) and 4-benzoylphenyl methacrylate. These functional groups may be provided on a polymer that comprises an antimicrobial or antithrombogenic group or on separate polyfunctional crosslinker molecules. For instance, the reactive groups may be placed on a backbone of polyethylene glycol, polyvinyl pyrrolidinone, polyacrylate, polymethylacrylate, or polyalkylene oxide. The crosslinker may be added to a solution of the polymer, or otherwise contacted with the polymer. Crosslinking will take place upon mixing or may be activated when desired, depending upon the particular chemistry involved. The polyfunctional crosslinker may be part of a melt or solution comprising the polymer, or added before, or after, such a polymer is contacted with a surface.

Embodiments may be made by the following process. In general, a backbone monomer that comprises the desired attachment group is reacted with the desired amine position on the antimicrobial precursor. The resulting product is a polymerizable group connected to an antimicrobial agent by an attachment group, forming an antimicrobial monomer. Similarly, a backbone monomer that comprises the desired attachment group is reacted with the desired amine or hydroxide position on the antithrombogenic precursor. The resulting product is a polymerizable group connected to an antithrombogenic agent by an attachment group, forming an antithrombogenic monomer. The antithrombogenic monomer and the antimicrobial monomer are then mixed together at the desired ratio and reacted by appropriate method to form a polymer comprising both antimicrobial and antithrombogenic agents. In some embodiments the desired molar ratio of the antithrombogenic monomer to the antimicrobial monomer is not more than 1:3, or not less than 1:25, or between about 1:3 and 1:25. In further embodiments the desired molar ratio of the antithrombogenic monomer to the antimicrobial monomer is between about 1:6 and 1:25, or between about 1:3 and 1:20, or between about 1:6 and 1:20. A person of ordinary skill in the art will recognize that additional ranges are contemplated and are within the present disclosure. Artisans will immediately appreciate that all values and ranges within the expressly stated limits are contemplated, e.g., about. In further embodiments the antimicrobial monomer and the antithrombogenic monomer are polymerized separately and then blended together in the desired ratios described above.

In some embodiments polymerization occurs through a free radical process. In general the antithrombogenic monomer or the antimicrobial monomer is mixed with one or more co-monomers, degassed, and heated to the reaction temperature. The reaction temperature may be above about 60° C., or from about 60° C. to about 80° C. or from about 65° C. to about 75° C. The polymerization initiator (for example potassium persulfate) is then added followed by the missing antithrombogenic monomer or antimicrobial monomer. The reaction is allowed to progress for a determined amount of time and then is quenched. The reaction may be allowed to progress for at least 20 minutes, for about 20 minutes to about 40 minutes, for about 25 minutes to about 30 minutes, for no more than about 90 minutes, or for no more than about 60 minutes. The resulting polymer is then purified. A person of ordinary skill in the art will recognize that additional ranges are contemplated and are within the present disclosure. Artisans will immediately appreciate that all values and ranges within the expressly stated limits are contemplated, e.g., about.

In further embodiments the antimicrobial and antithrombogenic monomers may be polymerized separately. In general the antimicrobial monomer is mixed with one or more co-monomers, degassed, and heated to the reaction temperature. The polymerization initiator is then added. The reaction is allowed to progress to a desired viscosity and then is quenched. The resulting polymer is then purified. The antithrombogenic monomer is mixed with one or more co-monomers, degassed, and heated to the reaction temperature. The reaction temperature may be above about 60° C., from about 60° C. to about 80° C. or from about 65° C. to about 75° C. The polymerization initiator (for example potassium persulfate) is then added. The reaction is allowed to progress to a desired viscosity and then is quenched. The resulting polymer is then purified. The two polymers are then blended together in a desired ratio. A person of ordinary skill in the art will recognize that additional ranges are contemplated and are within the present disclosure. Artisans will immediately appreciate that all values and ranges within the expressly stated limits are contemplated, e.g., about.

In some embodiments the antimicrobial precursor is a compound comprising a biguanide group with the desired amine position being a part of the biguanide group. In such embodiments the antimicrobial precursor may be a hydrochloride salt comprising a biguanide group. The salt may first be neutralized with a strong base. The biguanide group is then reacted with a backbone monomer that comprises the desired attachment group, as shown in Reaction Scheme 1 below. In further embodiments the antimicrobial precursor is a compound comprising a biguanide group with the desired amine position being a primary amine, cyanoamine, or cyanoguanidine group that is not part of the biguanide group. In such embodiments the antimicrobial precursor may be a hydrochloride salt comprising a biguanide group. The precursor is reacted with a backbone monomer that comprises the desired attachment group without first neutralizing the salt, as shown in Reaction Scheme 2 below.

In some embodiments the antithrombogenic precursor is a compound comprising a heparin group, with the heparin group comprising a hydroxide or a primary amine. In such embodiments the antithrombogenic precursor is reacted with an activated backbone monomer that comprises the desired attachment group, as shown in Reaction Scheme 3. The heparin group may by complexed with benzalkonium prior to the reactions. If the heparin group is complexed it may be decomplexed prior to use as a coating. The backbone monomer may be activated by reacting with an amide, as shown in Reaction Scheme 3.

Reaction Scheme 1: Reaction on the biguanide group

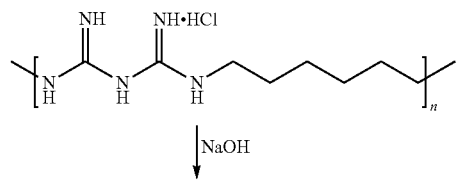

13    14
-continued
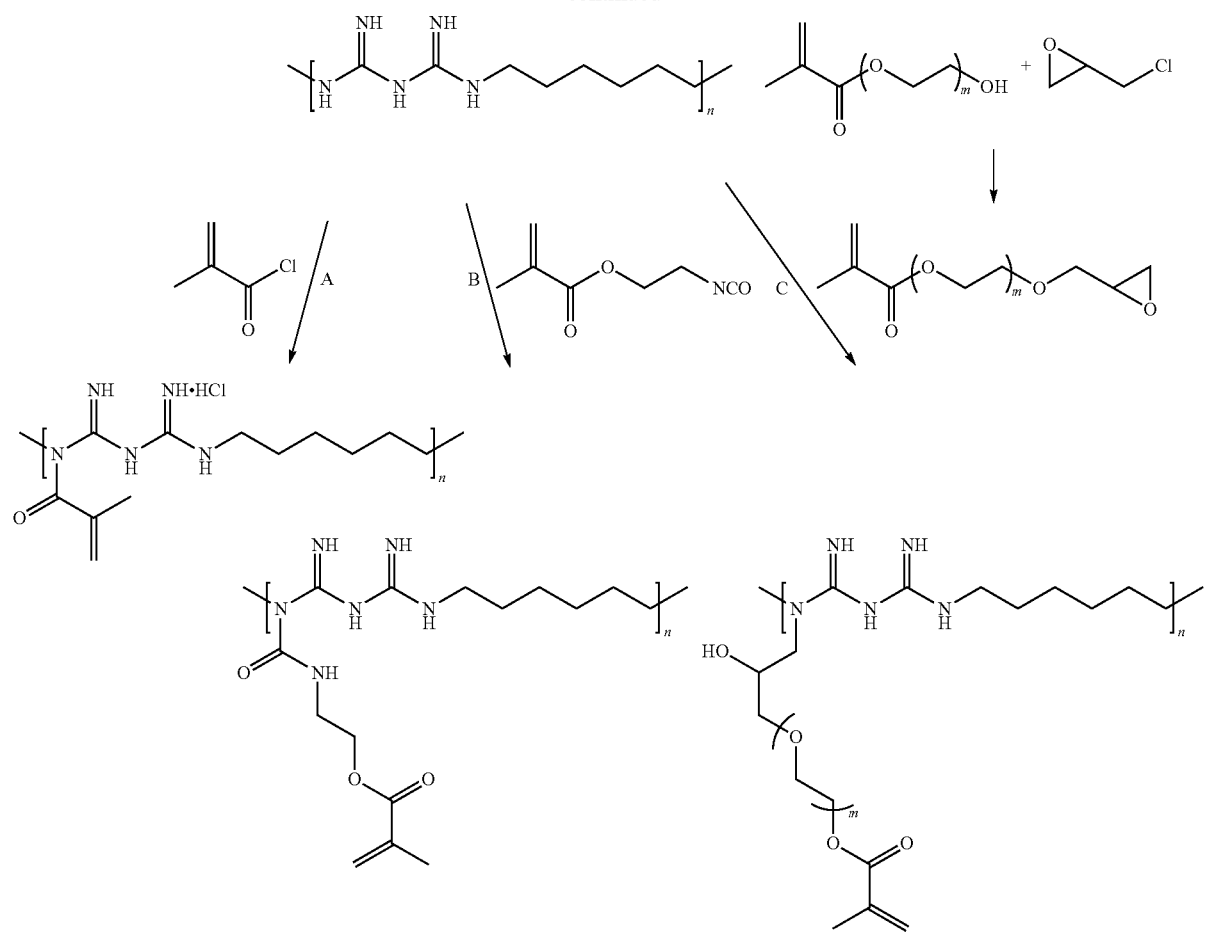
Reaction Scheme 2: Reaction on the primary amine end group
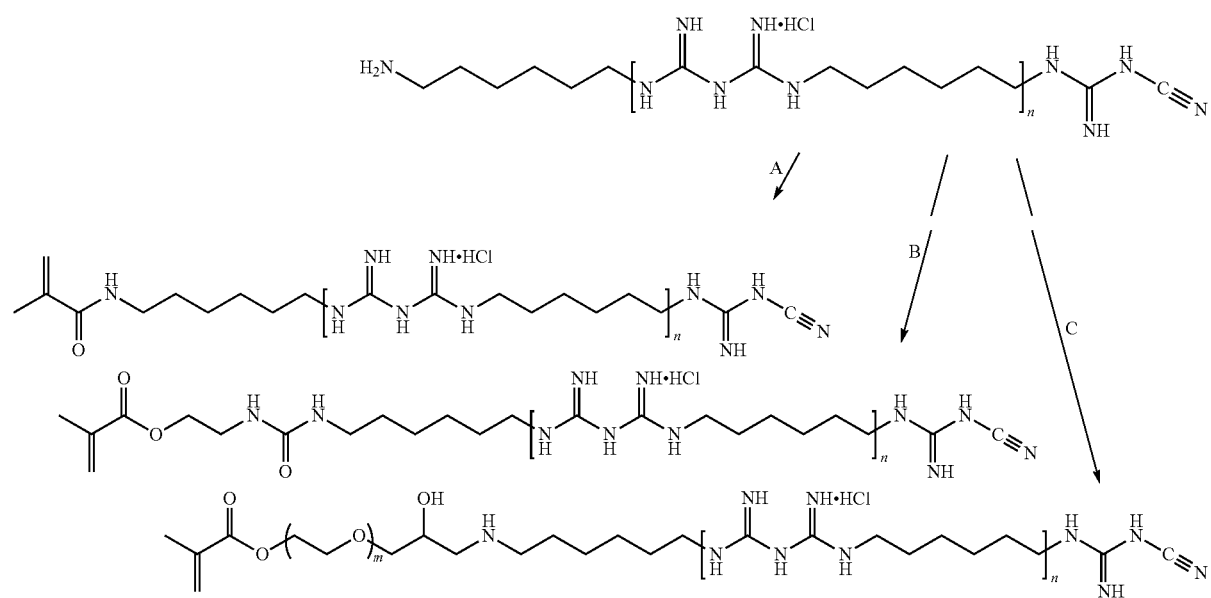

Reaction Scheme 3: Reaction of the heparin

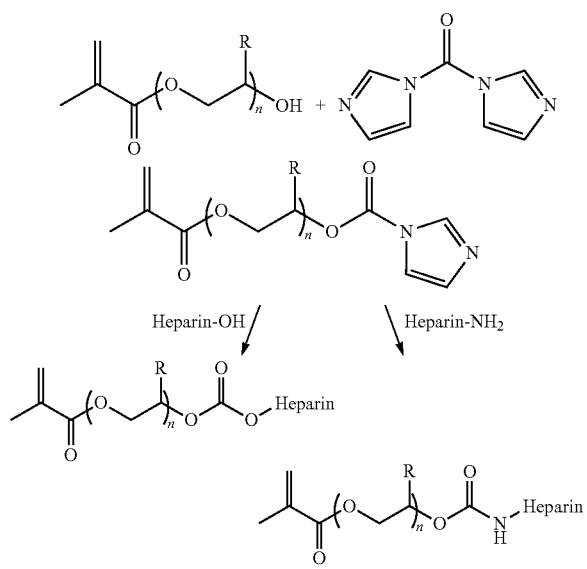

A coating is a substance that provides complete or partial coverage of an item. A coating may be a single layer or may be more than one layer with each layer comprising the same compound or different compounds. In some embodiments, the coating will have only one layer with the antimicrobial/antithrombogenic polymer or polymer blend along with any other desired compounds. The layer may consist essentially of the antimicrobial/antithrombogenic polymer or polymer blend. In further embodiments the coating will have multiple layers with at least one layer consisting essentially of the antimicrobial/antithrombogenic polymer or polymer blend. When a layer consists essentially of the polymer or polymer blend, the polymer or polymer blend is at least about 90% of the layer by weight. In some embodiments the polymer or polymer blend may be at least about 93%, 95%, or 97% of the layer by weight. A person of ordinary sill in the art will recognize that additional ranges are contemplated and are within the present disclosure. Artisans will immediately appreciate that all values and ranges within the expressly stated limits are contemplated, e.g., about.

In some embodiments, it may be desirable to polymerize the polymer compounds described herein with the material of the medical device directly. In other embodiments, the copolymers can be dissolved in solution to be coated onto medical devices using any suitable solution coating method, including, dip-coating, spray coating (ultrasonic, electrostatic, thermal), dip-coating with UV cure, or dip-coated and cross-linked with a polyfunctional cross-linker (e.g. polyaziridines, polyisocyanates).

Suitable medical apparatus for coating include medical devices such as contact lenses, catheters for vascular access (both arterial and venous), abdominal cavity tubing, drainage bags and connectors of various kinds, catheters, blood bags, dialysis or other membranes, surgical gloves, surgical instruments, vascular grafts, stents, contact lenses and intra-ocular lenses, contact lens cases, bottles, diagnostic apparatus, oxygenators, heart valves and pumps, artificial blood vessels, cardiac stents, venous stents, arterial stents, kidney stents, ureter stents, cardiac valve leaflets, shunts, cardiac devices including pacemakers, transcutaneous catheters, dialysis ports, or ports for chemotherapy.

In some embodiments the polymers may comprise additional pendant groups or co-monomers and/or may be blended with other polymers or compounds to give the coatings additional beneficial properties. These additional compounds and pendant groups include lubricants, hydrophilic compounds and pendant groups, non-fouling compounds, therapeutic agents, and crosslinkers.

Examples of co-monomers can be found in US Publication No. 2011/0274821 "Heparin Coatings" to Luthra et al., which is hereby incorporated by reference herein in its entirety to the extent it does not contradict what is explicitly disclosed herein. Monomers for mixing with the polysaccharide macromers can include, but are not limited to, monomers with hydroxyl groups (e.g., hydroxyethyl methacrylate), monomers with glycerol groups (e.g., glycerol monomethacrylate, glycerol dimethacrylate, glycerol trimethacrylate), monomers with polyoxyalkylene ether groups (e.g., polyethylene glycol methacrylate, polypropylene glycol methacrylate), monomers with vinyl groups (e.g., N-vinyl pyrrolidone), monomers. With zwitterionic groups (e.g., 2-methacryloyloxyethyl-2-(trimethyl ammonium) phosphate, monomers with silicone groups (e.g., methacryloxypropyl tris(trismethyl-siloxy)silane and other silicone methacrylate or acrylates), monomers having sulphate groups (e.g., vinyl sulphonic acid), monomers having sulphonate groups (e.g., ammonium sulphatoethyl methacrylate), heparin monomer as cited in the patent PCT GB 9701173 and U.S. Pat. No. 6,096,798, which are hereby incorporated by reference herein in their entirety to the extent they do not contradict what is explicitly disclosed herein, glycerol monomethacrylate, and biocompatible ampholyte monomers containing phosphate and amine moieties, such as those described in U.S. Publication No. 2013/0053470, which is hereby incorporated by reference herein in its entirety to the extent it does not contradict what is explicitly disclosed herein.

Lubricants as a class are a group or moiety that reduces the coefficient of friction. Examples of suitable lubricants can be found in U.S. Pat. No. 6,287,707 "Biocompatible Lubricious Hydrophilic Materials for Medical Devices" to Luthra et al., which is hereby incorporated by reference herein in its entirety to the extent it does not contradict what is explicitly disclosed herein. On suitable lubricant disclosed therein is a biocompatible, lubricious, hydrophilic material comprising a terpolymer of 5 to 25 mole percent of a polymerizable monomer (1) having a polyethylene oxide unit with an average degree of polymerization from 5 to 18 and a polymerizable carbon-carbon double bond, 5 to 30 mole percent of a polymerizable monomer (2) having a polyethylene oxide unit with an average degree of polymerization from 19 to 65 and polymerizable carbon-carbon double bond, and 45 to 90 mole percent of an alkyl methacrylate (3):

(1)
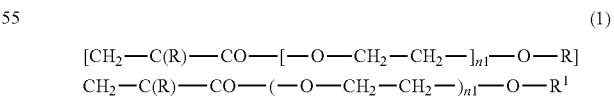

where n1 is from 5 to 18, and [each] R and $R^1$ are [is] independently H or $CH_3$ (2)
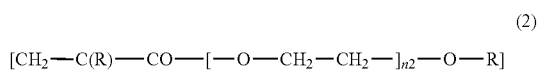

-continued

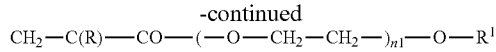

where n2 is from 19 to 65, and [each] R and $R^1$ are [is] independently H or $CH_3$

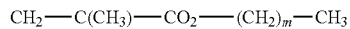
(3)

where m is from 3 to 17. Monomers (1) and (2) are hydroxy or, preferably, methoxy polyethyleneglycol acrylates or, preferably, methacrylates, and provide the hydrophilic moieties in the terpolymer. Monomer (3), ranging from butyl to octadecyl methacrylate, provides the hydrophobic moieties. The preferred molar proportions of (1), (2) and (3) are about 15% each of (1) and (2) and 70% of (3). In weight terms, proportions of 6 to 20% of (1), 40 to 80% of (2) and 10 to 50% of (3) are generally appropriate. It is preferred that monomer (1) has polyethylene oxide units with a degree of polymerization n1 from 5 to 12, more especially a degree of polymerization n1 from 5 to 10. It is preferred that monomer (2) has polyethylene oxide units with a degree of polymerization n2 from 20 to 50, more especially a degree of polymerization n2 from 22 to 48. It is preferred that monomer (3) is n-butyl methacrylate. Further suitable lubricants include N-vinylpyrrolidone, glycerol, glycerol methacrylate, glycols, polyethylene glycol methacrylate, phosphoryl choline, and derivatives thereof.

Hydrophilic groups are well known in the art, and the term is well understood. Examples of suitable hydrophilic groups and compounds can be found in U.S. Publication No. 2013/0053470 "Biocompatible, Biomimetic Ampholyte Materials" to Raisin-Dadre et al., which is hereby incorporated by reference herein in its entirety to the extent it does not contradict what is explicitly disclosed herein. For example, an ampholyte compound represented by the general formula:

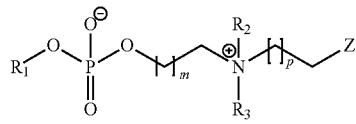
General wherein R1, R2, and R3 are independently chosen from the group consisting of
(a) an alkyl group,
(b) an aryl group,
(c) a cycloalkyl group,
(d) a cycloalkenyl group,
(e) a heterocycle group, and
(f) an alkenyl group, wherein m and p independently range from 0 to 13, with an m of 1 to 13 denoting a hydrocarbon chain referred to as the m-hydrocarbon chain and a p in a range from 1 to 13 denoting a hydrocarbon chain referred to as the p-hydrocarbon chain and wherein Z represents (a) a carbon with a double bond to the compound (b) a group represented by a general formula of

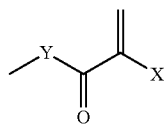

wherein X represents a hydrogen or a methyl, and Y represents an oxygen in an ester moiety or a secondary amine in an amide moiety. Further suitable hydrophilic groups include N-vinyl pyrrolidone, glycerol, glycerol methacrylate, glycols, polyethylene glycol methacrylate, phosphoryl choline, and derivatives thereof.

Non-fouling compounds prevent the laying down and adhesion of biological and chemical entities on to a surface. Suitable non-fouling compounds include (poly(ethylene glycol) and methoxy ether poly(ethylene glycol)), methacryloyloxyethyl phosphorylcholine, and 2-((2-(methacryloyloxy)ethyDdimethylammonio)ethyl 2-methoxyethyl phosphate).

Therapeutic agents can be blended with the polymer coating to allow for the localized delivery of compounds.

In some embodiments the anti-microbial monomer takes the structure depicted in structures 1-4 below. In some embodiments of structures 1-4, n is from 1 to 30, p is from 1 to 10000. X is a methyl or hydrogen. In further embodiments n may be from 5 to 15. In further embodiments p may be from 5 to 50. These ranges may be combined.

Structure 1
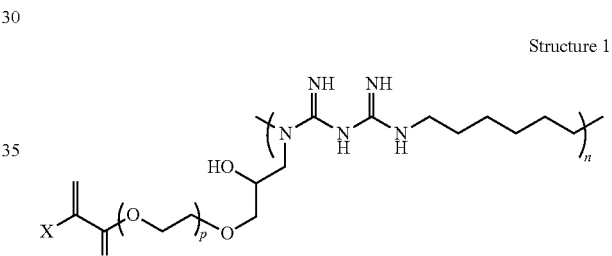

Structure 2
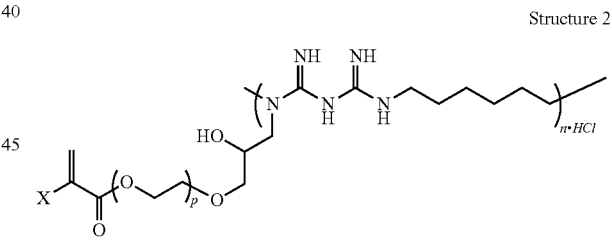

Structure 3
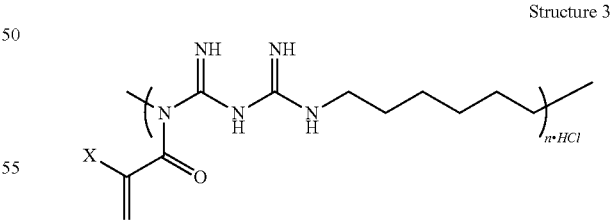

Structure 4
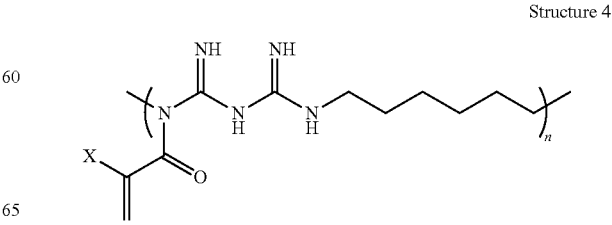

In some embodiments the anti-microbial monomer takes the structure depicted in structure 5. In some embodiments of structure 5, n is from 1 to 30, m is from 1 to 10000. X is a methyl or hydrogen. In further embodiments n may be from 5 to 15. In further embodiments m may be from 3 to 6. These ranges may be combined.

Structure 5

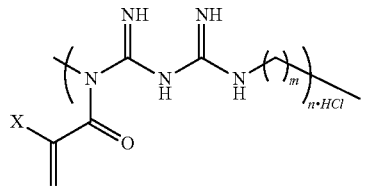

In some embodiments the anti-microbial monomer takes the structure depicted in structure 6. In some embodiments of structure 6, n is from 1 to 30, m is from 1 to 10, and p is from 1 to 10000. X is a methyl or hydrogen. In further embodiments n may be from 5 to 15. In further embodiments m may be from 3 to 6. In further embodiments p may be from 5 to 50. These ranges may be combined.

Structure 6

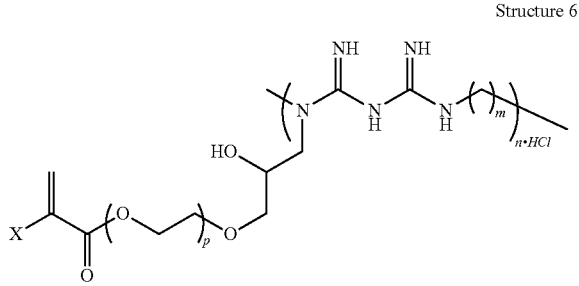

In some embodiments the anti-microbial monomer takes the structure depicted in structure 7. In some embodiments of structure 7, n is from 1 to 30, m is from 1 to 10, and r is from 0 to 10. X is a methyl or hydrogen. In further embodiments n may be from 5 to 15. In further embodiments m may be from 3 to 6. In further embodiments r may be from 2 to 5. These ranges may be combined.

Structure 7

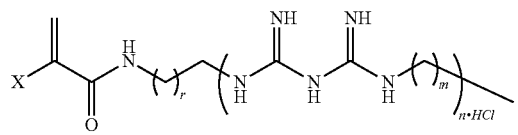

In some embodiments the anti-microbial monomer takes the structure depicted in structure 8. In some embodiments of structure 8, n is from 1 to 30, m is from 1 to 10, p is from 1 to 10000, and r is from 0 to 10. X is a methyl or hydrogen. Y is a substituted or unsubstituted hydrocarbon chain that may or may not contain heteroatoms. In further embodiments n may be from 5 to 15. In further embodiments m may be from 3 to 6. In further embodiments p may be from 5 to 50. In further embodiments r may be from 2 to 5. These ranges may be combined.

Structure 8

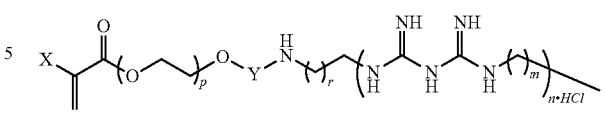

In some embodiments the anti-microbial monomer takes the structure depicted in structure 9. In some embodiments of structure 9, n is from 1 to 30, m is from 1 to 10, r is from 0 to 10, and s is from 0 to 20. X is a methyl or hydrogen. In further embodiments n may be from 5 to 15. In further embodiments m may be from 3 to 6. In further embodiments r may be from 2 to 5. In further embodiments s may be from 1 to 5. These ranges may be combined.

Structure 9

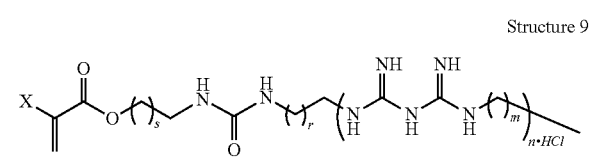

In some embodiments the anti-microbial monomer takes the structure depicted in structure 10. In some embodiments of structure 10, n is from 1 to 30, m is from 1 to 10, and s is from 0 to 20. X is a methyl or hydrogen. In further embodiments n may be from 5 to 15. In further embodiments m may be from 3 to 6. In further embodiments s may be from 1 to 5. These ranges may be combined.

Structure 10

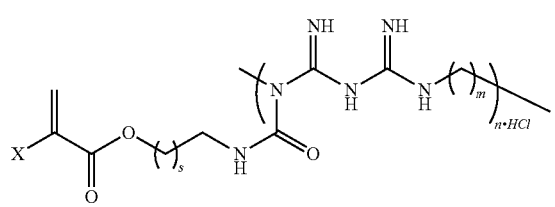

In some embodiments the anti-microbial group takes the structure depicted in structures 11 and 12 below. In some embodiments of structures 11 and 12, n is from 1 to 30. In some embodiments of structures 11 and 12 m is a hydrocarbon chain of 1 to 6 carbons. The chain may or may not be substituted. In some embodiments of structures 11 and 12 p is a hydrocarbon chain of 1 to 6 carbons. The chain may or may not be substituted. In further embodiments n may be from 5 to 15. The embodiments of structures 11 and 12 may be derivatized with a linker and a methacrylate functionality on the guanide functionality or at the chain end. These ranges may be combined.

Structure 11

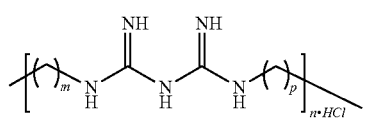

-continued

Structure 12

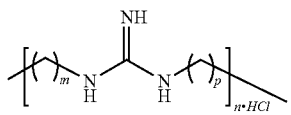

In some embodiments the anti-microbial monomer takes the structure depicted in structure 13 and 14. In some embodiments of structure 13 and 14, n is from 1 to 30. X is a methyl or hydrogen. Y is a substituted or unsubstituted hydrocarbon chain that may or may not contain heteroatoms. In certain embodiments Y may be omitted entirely. In further embodiments n may be from 5 to 15. These ranges may be combined.

Structure 13

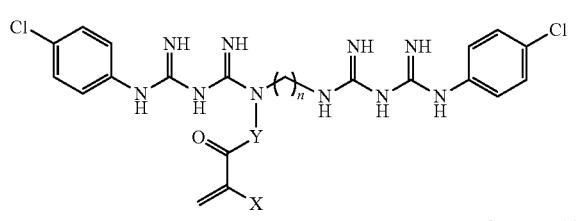

Structure 14

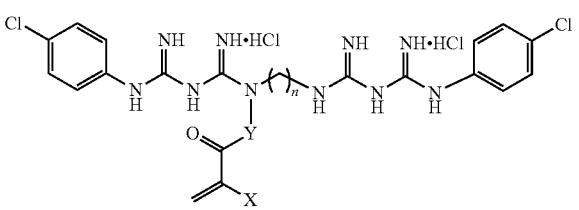

In some embodiments the antithrombogenic monomer takes the structure depicted in structure 15. In some embodiments of structure 15, n is from 1 to 10000. X is a methyl or hydrogen. Y is a heteroatom, a nitrogen, or an oxygen atom. $R_1$ and $R_2$ are substituted or unsubstituted hydrocarbon chains that may or may not contain heteroatoms. In certain embodiments Y may be omitted entirely. In further embodiments n may be from 5 to 50. In further embodiments Heparin may be benzalkonium heparin, heparin sulfate, heparan sulfate, heparin ammonium, heparin benzyl ester, heparin calcium, heparin lithium, heparin sodium. Heparin may be replaced by derivatives of heparin including heparin methacrylate, heparin quaternary ammonium salt complex methacrylate, heparin methacrylate salt, and heparin polyethylene glycol methacrylate or other glycosaminoglycans including dermatan sulfate, chondroitin sulfate, keratan sulfate, and hyaluronic acid.

Structure 15

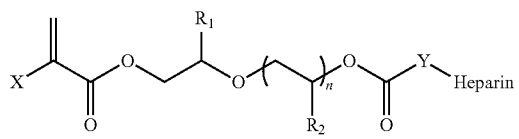

In some embodiments the antithrombogenic monomer takes the structure depicted in structure 16. X is a methyl or hydrogen. Y is a substituted or unsubstituted hydrocarbon chain that may or may not contain heteroatoms. In further embodiments Heparin may be benzalkonium heparin, heparin sulfate, heparan sulfate, heparin ammonium, heparin benzyl ester, heparin calcium, heparin lithium, heparin sodium. Heparin may be replaced by derivatives of heparin including heparin methacrylate, heparin quaternary ammonium salt complex methacrylate, heparin methacrylate salt, and heparin polyethylene glycol methacrylate or other glycosaminoglycans including dermatan sulfate, chondroitin sulfate, keratan sulfate, and hyaluronic acid.

Structure 16

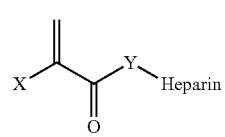

The following non-limited Examples illustrate different aspects of various embodiments of the invention.

EXAMPLES

Example 1

Synthesis of Heparin Poly(Ethylene Glycol) Methacrylate 1.25 g of carbonyl diimidazole (CDI) was dissolved in 10 mL anhydrous dichloromethane in a 100 mL conical flask. 2.5 g of poly(ethylene glycol) methacrylate was dissolved in 10 mL of anhydrous dichloromethane, the mixture was blended into a 25 mL dropping funnel and added drop wise to the CDI in the conical flask at room temperature over a period of approximately 1 hour. The mixture was left to stir for an additional 2 hours. Then, the dichloromethane was removed under rotary evaporation.

12.5 g of sodium heparin (12-14 kDa) was dissolved in 75 mL of pure water. In the conical flask, 30 mL of pure water was added to the CDI-activated poly(ethylene glycol) methacrylate from above. The mixture was then added to the aqueous solution of sodium heparin and left to stir at room temperature for 16 hours.

After the 16 hour period, the heparin mixture was precipitated twice in tetrahydrofuran and twice in acetone.

The poly(ethylene glycol) methacrylate-derivatized heparin was then dried in a vacuum oven in small pellets for 8 hours at~40-50° C.

Alternatively, the pH of the solution can be adjusted to 8.5-9 once the heparin and CDI-activated poly(ethylene glycol) methacrylate are mixed together. Then, the pH can be re-adjusted to 7 once the reaction is finished.

Example 2

Benzalkonium-heparin Complex 10 g of sodium heparin was dissolved in 60 mL of water. 30 g of benzalkonium chloride was dissolved in 100 mL water.

Once totally dissolved and cooled down, the benzalkonium chloride solution was added to the sodium heparin aqueous solution to precipitate the heparin-benzalkonium complex.

The white precipitate was stirred for 10 minutes and then left to stand.

The white precipitate was filtered and washed with water thoroughly in order to remove any water soluble starting materials.

The white precipitate was dissolved in isopropanol and re-precipitated in water, filtered and washed thoroughly with water.

The precipitate was suspended in water and dialysed in water at a molecular weight cut off of 3500 Daltons and then freeze-dried to recover a white powder of sodium heparin-benzalkonium complex.

The heparin poly(ethylene glycol) methacrylate from example 1 can also be complexed with benzalkonium chloride using the same method as above.

Example 3

Heparin-benzalkonium Complex, Decomplexed in Solution

The heparin poly(ethylene glycol) methacrylate-benzalkonium complex or heparin methacrylate-benzalkonium complex was introduced in an aqueous sodium chloride solution (2.1 M). Overtime, the solid dissolved. Once dissolved, the aqueous solution was precipitated from acetone and further washed with acetone to isolate the decomplexed heparin poly(ethylene glycol) methacrylate or heparin methacrylate.

The white precipitate was dried in a vacuum oven.

Example 4

Synthesis of poly(hexanide) methacrylate (PHMB-MA)

Poly(hexanide) hydrochloride was dialysed against water at a molecular weight cut off of 3500 Daltons. 130 g of dialysed poly(hexanide) in aqueous solution (~4 L of solution) was then neutralised with a solution of 1.98 g of sodium hydroxide dissolved in 220 mL of water. Aqueous sodium hydroxide was slowly added (1 L/min) to the aqueous dialysed poly(hexanide).

After the addition, the neutralised solution was frozen and ultimately freeze-dried to obtain a white powder of neutralised poly(hexanide).

50 g of neutralised poly(hexanide) was dissolved in 125 mL of water. 1.86 mL of methacryloyl chloride was added to the solution and left to stir for a minimum of 1 hour, until the pH was 5.5 and the solution was totally clear.

The aqueous mixture was precipitated twice in tetrahydrofuran and washed twice in acetone. The precipitate was dried in a vacuum oven at 50° C. for 8-12 hours to obtain a white powder.

Example 5

Synthesis of poly(ethylene glycol) methacrylate-poly(hexanide)

4.8 g of sodium hydroxide was dissolved in 40 mL of water. The mixture was stirred and left to cool down to room temperature.

40 g of poly(ethylene glycol) methacrylate was added to the above mixture and left to stir for ~2 hours.

17.4 mL of epichlorohydrin was blended in a flask and the poly(ethylene glycol) methacrylate solution from above was blended in a dropping funnel and slowly added to the flask containing epichlorohydrin. The addition was completed over a period of~2 hours 30 minutes.

The reaction mixture was then stirred at 45° C. for 16 hours.

After the 16 hour period, the water mixture was washed with diethyl ether via extraction. Then, the water layer was extracted with dichloromethane. The dichloromethane fraction was dried over a desiccant and the dichloromethane was evaporated using a rotary evaporator to yield a transparent oil of epoxy-poly(ethylene glycol) methacrylate.

57 g of neutralised poly(hexanide) (as per example 3) was dissolved in 240 mL of water. 10.8 g of the epoxy-poly (ethylene glycol) methacrylate was added to the neutralised poly(hexanide). The mixture was stirred at ~40° C. overnight (~16 hours).

After the 16 hour period, the mixture was precipitated twice in tetrahydrofuran and washed twice in acetone. The white paste was dissolved in a little amount of water, frozen and ultimately freeze-dried to obtain a white powder of poly(ethylene glycol) methacrylate poly(hexanide).

Example 6

Synthesis of chlorhexidine methacrylate 1 g of chlorhexidine was dissolved in 100 mL anhydrous dichloromethane. 153.4 mg (140 µL) of 2-isocyanatoethyl methacrylate was dissolved in 50 mL of anhydrous dichloromethane and was added drop wise to the chlorhexidine solution. Infrared was used to follow the disappearance of the isocyanate functionality. Once the isocyanate had totally disappeared, the dihydrochloride of the resulting product was formed by adding 0.99 mL of HCl (4M) in 1,4-dioxane. Then, the reaction mixture was evaporated to yield chlorhexidine dihydrochloride methacrylate.

1 g of chlorhexidine was dissolved in 100 mL, of anhydrous dichloromethane. 103.4 mg (97 µL) of methacryloyl chloride was dissolved in 10 mL of anhydrous dichloromethane and was added dropwise to the chlorhexidine solution. The reaction was left to stir for 3-4 hours. The dihydrochloride was formed by adding 0.99 mL of HCl (4M) in 1,4-dioxane. Then, the reaction mixture was evaporated to yield the chlorhexidine dihydrochloride methacrylate.

Chlorhexidine digluconate can be used instead of chlorhexidine.

Example 7

Synthesis of Combination Polymer (Using poly(ethylene glycol) methacrylate polyhexanide and a Low Dose of heparin methacrylate)

In a round-bottom flask, equipped with a condenser, a thermometer and a Pasteur pipette attachment to nitrogen inlet, 0.5 g of heparin poly(ethylene glycol) methacrylate (as per example 1) was dissolved in 28 mL of water. Subsequently, the following components were added into the flask: 13.5 g (solid) of methoxy poly(ethylene glycol) methacrylate of MW 2000, purified on charcoal and diluted at 20% (w/v), 2.98 g of methoxy poly(ethylene glycol) methacrylate of MW 350, 1 mL of methacrylic acid, 5.98 g of butyl methacrylate and 15 mL of isopropanol. The reflux condenser was turned on, the nitrogen allowed to bubble into the mixture of monomers and the heating turned up to warm up the mixture of monomers.

In a separate vial, 1.6 g of poly(ethylene glycol) methacrylate-poly(hexanide) (from example 4) was dissolved in 5 mL of water. In yet another vial, 150 mg of potassium persulfate was dissolved in 4 mL of water and degassed with nitrogen.

Once the mixture had reached a temperature of 70° C., the potassium persulfate aqueous solution was added to the mixture of monomers in the round bottom flask and the polymerisation started.

The poly(ethylene glycol) methacrylate-poly(hexanide) aqueous solution was then added. The polymerisation was allowed to progress for a total of 25-30 minutes and was quenched by adding 25 mL of icy cold water. The polymerisation solution was allowed to cool down to room temperature and was dialysed at a molecular weight cut off of 12-14 KDa against water overnight.

Example 8

Synthesis of a Combination Polymer

The polymer from example 7 in which methacrylic acid is replaced by 4-benzoylphenyl methacrylate (150 mg) during the synthesis, or in which both methacrylic acid and 4-benzoylphenyl methacrylate are jointly used.

Example 9

Synthesis of Combination Polymer (Using poly(ethylene glycol) methacrylate poly(hexanide) and a High Dose of heparin methacrylate)

In a round-bottom flask, equipped with a condenser, a thermometer and a Pasteur pipette attachment to nitrogen inlet, 1.03 g of heparin poly(ethylene glycol) methacrylate (as per example 1) was dissolved in 28 mL of water. Subsequently, the following components were added into the flask: 13.5 g (solid) of methoxy poly(ethylene glycol) methacrylate of MW 2000, purified on charcoal and diluted at 20% (w/v), 3 g of methoxy poly(ethylene glycol) methacrylate of MW 350, 1 mL of methacrylic acid, 5.98 g of butyl methacrylate and 15 mL of isopropanol. The reflux condenser was turned on, the nitrogen allowed to bubble into the mixture of monomers and the heating turned up to warm up the mixture of monomers. In a separate vial, 1.6 g of poly(ethylene glycol) methacrylate-poly(hexanide) (from example 4) was dissolved in 5 mL of water. In yet another vial, 150 mg of potassium persulfate was dissolved in 4 mL of water and degassed with nitrogen.

Once the mixture had reached a temperature of 70° C., the potassium persulfate aqueous solution was added to the mixture of monomers in the round bottom flask and the polymerisation started.

The poly(ethylene glycol) methacrylate-poly(hexanide) aqueous solution was then added. The polymerisation was allowed to progress for a total of 25-30 minutes and was quenched by adding 25 mL of icy cold water. The polymerisation solution was allowed to cool down to room temperature and was dialysed at a molecular weight cut off of 12-14 KDa against water overnight.

Example 10

Synthesis of a Combination Polymer

The polymer from example 9 in which methacrylic acid is replaced by 4-benzoylphenyl methacrylate (150 mg) during the synthesis, or in which both methacrylic acid and 4-benzoylphenyl methacrylate are jointly used.

Example 11

Synthesis of Combination Polymer (Using poly(hexanide) methacrylate)

In a round-bottom flask, equipped with a condenser, a thermometer and a Pasteur pipette attachment to nitrogen inlet, 1 g of heparin poly(ethylene glycol) methacrylate (as per example 1) was dissolved in 28 mL of water. Subsequently, the following components were added into the flask: 13.5 g (solid) of methoxy poly(ethylene glycol) methacrylate of MW 2000, purified on charcoal and diluted at 20% (w/v), 2.98 g of methoxy poly(ethylene glycol) methacrylate of MW 350, 1 mL of methacrylic acid, 5.98 g of butyl methacrylate and 15 mL of isopropanol. The reflux condenser was turned on, the nitrogen allowed to bubble into the mixture of monomers and the heating turned up to warm up the mixture of monomers.

In a separate vial, 1.6 g of poly(hexanide) methacrylate (from example 3) was dissolved in 5 mL of water. In yet another vial, 150 mg of potassium persulfate was dissolved in 4 mL of water and degassed with nitrogen.

Once the mixture had reached a temperature of 70° C., the potassium persulfate aqueous solution was added to the mixture of monomers in the round bottom flask and the polymerisation started.

The poly(hexanide) methacrylate aqueous solution was then added. The polymerisation was allowed to progress for a total of 25-30 minutes and was quenched by adding 25 mL of icy cold water. The polymerisation solution was allowed to cool down to room temperature and was dialysed at a molecular weight cut off of 12-14 KDa against water overnight.

Example 12

Synthesis of a Combination Polymer Using chlorhexidine dihydrochloride methacrylate In a round-bottom flask, equipped with a condenser, a thermometer and a Pasteur pipette attachment to nitrogen inlet, 0.5 g of heparin poly(ethylene glycol) methacrylate (as per example 1) was dissolved in 28 mL of water. Subsequently, the following components were added into the flask: 13.5 g (solid) of methoxy poly(ethylene glycol) methacrylate of MW 2000, purified on charcoal and diluted at 20% (w/v), 2.98 g of methoxy poly(ethylene glycol) methacrylate of MW 350, 1 mL of methacrylic acid, 5.98 g of butyl methacrylate and 15 mL of isopropanol. The reflux condenser was turned on, the nitrogen allowed to bubble into the mixture of monomers and the heating turned up to warm up the mixture of monomers.

In a separate vial, 2 g of chlorhexidine dihydrochloride methacrylate was dissolved in 5 mL of isopropanol. In yet another vial, 150 mg of potassium persulfate was dissolved in 4 mL of water and degassed with nitrogen.

Once the mixture had reached a temperature of 70° C., the potassium persulfate aqueous solution was added to the mixture of monomers in the round bottom flask and the polymerisation started.

The chlorhexidine dihydrochloride methacrylate aqueous solution was then added. The polymerisation was allowed to progress for a total of 25-30 minutes and was quenched by adding 25 mL of icy cold water. The polymerisation solution was allowed to cool down to room temperature and was dialysed at a molecular weight cut off of 12-14 KDa against water overnight.

Example 13

Synthesis of a Combination Polymer (Using heparin poly(ethylene glycol) methacrylate/benzalkonium complex)

In a round-bottom flask, equipped with a condenser, a thermometer and a Pasteur pipette attachment to nitrogen inlet, 1.68 g of poly(ethylene glycol) methacrylate poly (hexanide) was blended with 13.5 g (solid) of methoxy poly(ethylene glycol) methacrylate of MW 2000, purified on charcoal and diluted at 20% (w/v), 2.54 g of methoxy poly(ethylene glycol) methacrylate of MW 350, 1.5 mL of methacrylic acid, 5.80 g of butyl methacrylate and 35 mL of isopropanol. The reflux condenser was turned on, the nitrogen allowed to bubble into the mixture of monomers and the heating turned up to warm up the mixture of monomers.

In a separate vial, 2 g of heparin poly(ethylene glycol) methacrylate/benzalkonium complex (as per example 2) was dissolved in 10 mL of isopropanol. In yet another vial, 145 mg of potassium persulfate was dissolved in 5 mL of water and degassed with nitrogen.

Once the mixture in the round bottom flask had reached a temperature of 70° C., the potassium persulfate aqueous solution was added to the mixture of monomers in the round bottom flask and the polymerisation started.

The heparin poly(ethylene glycol) methacrylate/benzalkonium complex solution was then added. The polymerisation was allowed to progress for approximately 1 hour and was then allowed to cool down to room temperature.

The heparin/benzalkonium complex, incorporated in the polymer backbone, can be decomplexed after coating on a device as described in example 23 or can be decomplexed in solution after polymerisation using a sodium chloride aqueous solution.

The polymerisation solution was dialysed at a molecular weight cut off of 12-14 KDa against water overnight.

Example 14

Synthesis of a Combination Polymer

The polymer from example 13 in which methacrylic acid is replaced by 4-benzoylphenyl methacrylate (150 mg) during the synthesis, or in which both methacrylic acid and 4-benzoylphenyl methacrylate are jointly used.

Example 15

Synthesis of an Antimicrobial Polymer

In a round-bottom flask, equipped with a condenser, a thermometer and a Pasteur pipette attachment to nitrogen inlet, 11.67 g of poly(ethylene glycol) methacrylate poly (hexanide) was blended and dissolved in 140.7 mL of water. 81 g (solid) of methoxy poly(ethylene glycol) methacrylate of MW 2000, purified on charcoal and diluted at 20% (w/v), was added with 16.21 g of methoxy poly(ethylene glycol) methacrylate of MW 350, 11.22 mL of methacrylic acid, 37.33 g of butyl methacrylate and 84.8 mL of isopropanol. The reflux condenser was turned on, the nitrogen allowed to bubble into the mixture of monomers and the heating turned up to warm up the mixture of monomers.

In a separate vial, 905 mg of potassium persulfate was dissolved in 24 mL of water and degassed with nitrogen.

Once the mixture in the round bottom flask had reached a temperature of 70° C., the potassium persulfate aqueous solution was added to the mixture of monomers in the round bottom flask and the polymerisation started.

The polymerisation was allowed to progress to the desired level of viscosity and was quenched by the addition of 100 mL of icy cold water. Once cooled down to room temperature, the polymerisation solution was dialysed at a molecular weight cut off of 12-14 KDa against water overnight.

Example 16

Synthesis of an Antimicrobial Polymer

The polymer from example 15 in which methacrylic acid is replaced by 4-benzoylphenyl methacrylate (900 mg) during the synthesis, or in which both methacrylic acid and 4-benzoylphenyl methacrylate are jointly used.

Example 17

Synthesis of an Anti-coagulant Polymer (with High Heparin Ratio)

In a round-bottom flask, equipped with a condenser, a thermometer and a Pasteur pipette attachment to nitrogen inlet, 5.52 g of heparin poly(ethylene glycol) methacrylate was blended and dissolved with 60 mL of water. 14.5 g (solid) of methoxy poly(ethylene glycol) methacrylate of MW 2000, purified on charcoal and diluted at 20% (w/v), was added to the flask with 3.5 g of methoxy poly(ethylene glycol) methacrylate of MW 350, 1.25 mL of methacrylic acid, 8 g of butyl methacrylate and 20 mL of isopropanol. The reflux condenser was turned on, the nitrogen allowed to bubble into the mixture of monomers and the heating turned up to warm up the mixture of monomers.

In a separate vial, 200 mg of potassium persulfate was dissolved in 5 mL of water and degassed with nitrogen.

Once the mixture in the round bottom flask had reached a temperature of 70° C., the potassium persulfate aqueous solution was added to the mixture of monomers in the round bottom flask and the polymerisation started.

The polymerisation was allowed to progress for approximately 1 hour to the desired level of viscosity and was then allowed to cool down to room temperature. The polymerisation solution was dialysed at a molecular weight cut off of 12-14 KDa against water overnight.

Example 18

Synthesis of an Anti-coagulant Polymer (with Low Heparin Ratio)

In a round-bottom flask, equipped with a condenser, a thermometer and a Pasteur pipette attachment to nitrogen inlet, 1.5 g of heparin poly(ethylene glycol) methacrylate was blended and dissolved with 37 mL of water. 14.5 g (solid) of methoxy poly(ethylene glycol) methacrylate of MW 2000, purified on charcoal and diluted at 20% (w/v), was added to the flask with 3.5 g of methoxy poly(ethylene glycol) methacrylate of MW 350, 1.25 mL of methacrylic acid, 8 g of butyl methacrylate and 18 mL of isopropanol. The reflux condenser was turned on, the nitrogen allowed to bubble into the mixture of monomers and the heating turned up to warm up the mixture of monomers.

In a separate vial, 200 mg of potassium persulfate was dissolved in 5 mL of water and degassed with nitrogen.

Once the mixture in the round bottom flask had reached a temperature of 70° C., the potassium persulfate aqueous solution was added to the mixture of monomers in the round bottom flask and the polymerisation started.

The polymerisation was allowed to progress for approximately 1 hour to the desired level of viscosity and was then allowed to cool down to room temperature. The polymerisation solution was dialysed at a molecular weight cut off of 12-14 KDa against water overnight.

Example 19

Synthesis of an Anticoagulant Polymer

The polymers from examples 17 and 18 in which methacrylic acid is replaced by 4-benzoylphenyl methacrylate (150 mg) during the synthesis, or in which both methacrylic acid and 4-benzoylphenyl methacrylate are jointly used.

Example 20

Synthesis of an Anti-coagulant Polymer

The polymers from examples 17, 18, and 19 in which heparin poly(ethylene glycol) methacrylate may be replaced by benzalkonium-heparin methacrylate complex or benzalkonium-heparin poly(ethylene glycol) methacrylate complex.

Example 21

Coating Using the Combination Polymer, Heat-cured

A formulation was prepared as follows (% volume):

| | |
|---|---|
| Polymer solution from example 9 | 35.8% |
| IPA | 19% |
| Polyaziridine crosslinker solution at 10% | 0.8% |
| THF | 44.4% |

The device was dip-coated in the coating formulation, the film was left to dry at room temperature for approximately 20 minutes and then was cured at 70° C. for 1 hour.

Example 22

Coating Using the Combination Polymer, UV Cured

A formulation was prepared as follows (% volume):

| | |
|---|---|
| Polymer solution from example 10 | 35.8% |
| IPA | 19% |
| Polyaziridine crosslinker solution at 10% | 0.8% |
| THF | 44.4% |

The device was dip-coated in the coating formulation, the film was left to dry at room temperature for approximately 20 minutes. The film was firstly cured using UV light (360 seconds), followed by a 1 hour cure at 70° C. to provide a strong and stable coating.

Example 23

Coating Using the Complexed Combination Polymer

| | |
|---|---|
| Polymer solution from example 13 | 39.6% |
| IPA | 18% |
| Polyaziridine crosslinker solution at 10% | 0.5% |
| THF | 41.9% |

The device was dip-coated in the coating formulation, the film was left to dry at room temperature for approximately 20 minutes and then was cured at 70° C. for 1 hour.

The coated device was then left in a phosphate buffered saline solution for 5 min to decomplex the salt, then rinse in water thoroughly to remove any remaining salt.

Example 24

Coating Using a Blend of Antimicrobial Polymer and Anti-coagulant Polymer, Respectively 90/10% (w/v of the Final Concentration)

In a Falcon tube, 2.75 mL of isopropanol was blended with 6.42 mL of tetrahydrofuran. 4.2 mL of the antimicrobial polymer from example 11 was blended with 0.63 mL of the anticoagulant polymer from example 12. 100 µL of polyaziridine crosslinker at 10% (w/v) was added, the solution was mixed well and left to settle.

The device was dip-coated in the coating formulation, the film was left to dry at room temperature for approximately 20 minutes and then was cured at 70° C. for 1 hour.

Example 25

Coating Using a Blend of Antimicrobial Polymer and Anti-coagulant Polymer, Respectively 75/25% (w/v of the Final Concentration)

In a Falcon tube, 2.68 mL of isopropanol was blended with 6.26 mL of tetrahydrofuran. 3.5 mL of the antimicrobial polymer from example 15 was blended with 1.56 mL of the anticoagulant polymer from example 12. 100 µL of polyaziridine crosslinker at 10% (w/v) was added, the solution was mixed well and left to settle.

The device was dip-coated in the coating formulation, the film was left to dry at room temperature for approximately 20 minutes and then was cured at 70° C. for 1 hour.

Example 26

Coating Using the Antimicrobial Polymer

In a Falcon tube, 3 mL of isopropanol was blended with 7 mL of tetrahydrofuran. 4 mL of the antimicrobial polymer from example 15 was added and 100 µL of polyaziridine crosslinker at 10% (w/v) was added, the solution was mixed well and left to settle.

The device was dip-coated in the coating formulation, the film was left to dry at room temperature for approximately 20 minutes and then was cured at 70° C. for 1 hour Example 27

Coating Using the Anti-coagulant Polymer

In a Falcon tube, 3 mL of isopropanol was blended with 7 mL of tetrahydrofuran. 4 mL of the anticoagulant polymer from example 17 was added and 100 µL, of polyaziridine crosslinker at 10% (w/v) was added, the solution was mixed well and left to settle.

The device was dip-coated in the coating formulation, the film was left to dry at room temperature for approximately 20 minutes and then was cured at 70° C. for 1 hour.

Example 28

Methodology of Testing—Antimicrobial Proliferation/Microbial Adhesion

Test pieces are exposed to a particular medium (to enable protein adhesion etc.) such as plasma, blood or urine etc. for a predetermined time point, pieces are then washed then put into the test protocol. The test protocol effectively incubated the device with live microorganisms, washed device to removed "solution present bacteria", allowed active component sufficient time to "kill" then transferred to growth media where viable microorganisms on the device will proliferate into daughter cells in solution hence increasing turbidity of growth media which can then be measured by optical density.

Protocol

Day 1

Colonies of each relevant bacteria (Oxoid, UK) were transferred from cultures on agar slopes (Oxoid, UK) to tryptone soya broth (TSB) (Oxoid, UK) and incubated at 37° C. overnight. A second, bacteria-free control volume was also incubated at 37° C.

Day 2

Bacterial cultures and cultured controls were checked for turbidity, this was observable in cultures but controls were unclouded. A volume of 10% (v/v) TSB in isotonic saline was prepared in a sterile container and placed at 37° C.

Following this the coated and uncoated articles (cut to suitable assay dimensions as necessary) were placed in fresh de-ionised sterile water (Baxter, UK) for 30 mins at ambient temperature to hydrate the coating. Where the article was a tube, such as a catheter, the lumens were flooded using a disposable syringe (Midmeds, UK) which remained attached to the article throughout the hydration process. All handling of test surfaces was performed with sterile tweezers.

During the hydration stage the population density (CFU/ml) of each culture was assessed using a process akin to the McFarland Turbidity Standards, read at 600 nm. Once the absorbance was read, an appropriate volume of $5\times10^5$ CFU/ml bacterial suspension was prepared in the 10% (v/v) TSB. This challenge suspension is then transferred to sterile glass/plasticware of appropriate dimensions/volume to accommodate the test article.

The test articles were then rinsed with deionised sterile water and placed in the challenge suspension. Again, where the article is a tube, care is taken to ensure the exposure of the lumens. The test articles are then incubated for 60 mins at 37° C. Gentle manual agitation was applied at 30 mins to dislodge any bubbles that formed on the device surface.

Following the challenge incubation, articles were removed from the suspension and rinsed thoroughly with isotonic saline. Where secondary articles such as syringes or needles were attached to the test items, these were discarded and if necessary replaced with fresh sterile items. Where the test item is a tube such as a catheter, a 20 ml disposable syringe (plunger removed) is used as a funnel to rinse the lumens.

The test articles are then placed in an isotonic saline "soak" for 30 mins at ambient temperature, then rinsed a second time, and placed in a second soak for 60 mins, during which time a volume of 50% (v/v) TSB in isotonic saline was prepared, measured out into culture dishes (6-24 well as appropriate for the test item in question) (Griener Bio-One, UK) and brought to ambient temperature. A number of wells containing 50% TSB were reserved as device-free controls. After the second soak, test articles were subjected to a final rinse. Where secondary articles were present they were again discarded. Following this rinse the test items were either transferred whole to the 50% TSB solutions, or if appropriate cleaved into sections (using sterile razor blades and sterile foil) and these sections then transferred into the 50% TSB solution. When the items were cleaved into sections, the uppermost and lowermost sections were discarded. Where the test articles were tubes, a 20-200 µl pipette (Eppendorf, UK) and sterile tips (Griener Bio-One, UK) were used as necessary to flush air bubbles from the lumens of the sections immersed in 50% TSB.

The test items and device-free control wells are incubated at ambient temperature overnight.

Day 3

The culture plates containing the test items were visually examined for signs of growth in either the test item wells, or the control (device-free) wells. The plates were then sealed with film and placed at 37° C., and assessed visually ever hour for signs of growth. Turbidity typically presented after >4 hours at 37° C. after overnight incubation at RT, though inter-species and inter-device variation did occur). When wells containing uncoated articles exhibited strong signs of bacterial growth their contents were resuspended fully using disposable Pasteur pipettes, and then 300 µl transferred from each well to 96 well plates (in triplicate) before the plate(s) were read at 600 nm.

Example 29

Methodology of Testing—Platelet Adhesion to Device

Test pieces may (or may not be) exposed to a particular medium (to enable protein adhesion etc) such as plasma, blood or urine etc for a predetermined time point, pieces are then washed then put into the test protocol.

Venous blood was collected from healthy human volunteers (who denied taking any medication for six weeks). Briefly, after venipuncture, 2.5 ml of blood was collected and discarded. 10 ml of blood was then collected and anticoagulated using citrate phosphate dextrose (CPD) This was then split into two aliquots of 5 mL and of 5 mL of platelet rich plasma (PRP) and platelet poor plasma (PPP) were prepared by centrifugation. The platelet count was then taken using a haemocytometer and light microscope utilising phase contrast.

The PRP was then adjusted to $1\times10^5$ platelets/µL using PPP as a diluent.

For the experiments 200 µL of the $1\times10^5$ platelets/µL PRP from above was transferred to the middle of coated coverslip and left (covered to prevent evaporation) at 37° C. for half an hour. After this time point the slides were then rinsed three times in saline then fixed overnight in 2.5% glutaric dialdehyde (Sigma Aldrich) in PBS (Sigma Aldrich). They were then examined by light microscopy at ×2000 and the amount of platelets in the field of view counted.

Demonstrative photos were then taken using an inverted microscope and camera (both Motic Instruments).

Example 30

Methodology of Testing—Heparin Activity of Coated Surface

Test pieces may (or may not be) exposed to a particular medium (to enable protein adhesion etc) such as plasma, blood or urine etc for a predetermined time point, pieces are then washed and put into the test protocol.

Using a commercially available anti-IIa heparin kit (Hyphen Biomed via UK distributor Quadratech Diagnostics) the heparin activity of the device surface was measured via anti IIa inhibition.

Briefly; using a heparin reference material (Celsius laboratories) a calibration curve of heparin was prepared in physiological saline (9 g/L NaCl (Sigma Aldrich)) containing 1% Bovine Serum Albumin ("BSA" Sigma Aldrich), as shown in Table 1.

TABLE 1

|  | Heparin (U/ml) | | | | | |
| --- | --- | --- | --- | --- | --- | --- |
|  | 0 | 0.5 | 1 | 2 | 4 | 6 |
| mU of Heparin (if 100 μL is used in test) | 0 | 50 | 100 | 200 | 400 | 600 |

The reagents were then made as to the manufacturer's instructions and the test started (as per the manufacturer's instructions).

To a series of test tubes at 37° C., the following was added:

100 μL of calibrant or test piece (1 cm2) and 100 ul of 1% BSA in saline (i.e. 0 U/ml or 0 mU)

100 μL of Antithrombin (200 ug/ml)

500 μL of Assay Reaction Buffer

200 μL of Thrombin Substrate

This was then mixed and incubated at 37° C. for 2-3 minutes then 200 μL Human Thrombin (Preincubated at 37° C.) was added. This was then mixed and incubated at 37° C. for exactly 5 minutes. Reaction was then stopped using Citric Acid (20 g/L Sigma Aldrich). The acid was mixed in then absorbance at 405 nm was measured on a spectrophotometer (Perkin Elmer) against a blank prepared by mixing the above reagents in reverse order. A calibration curve was then prepared and linear regression was used for interpolation of heparin level on surface (acceptable if $r^2 > 0.98$).

Example 31

Activity of Combination Polymer and Antimicrobial Polymer (Coated on Polyurethane Haemodialysis Catheters) Against *Pseudomonas aeruginosa*

Catheters were coated as per the methodology set out in the relevant example (i.e. examples 21-27) and then tested for antimicrobial activity against *Pseudomonas aeruginosa* as per example 28.

The turbidity results obtained are shown below in Table 2 and FIG. 4.

TABLE 2

| Coating | Mean Optical Density (OD) (600 nm) | SD |
| --- | --- | --- |
| Uncoated Dual Lumen 14Fr Polyurethane Dialysis Catheter | 0.05825 | 0.00783 |
| Antimicrobial Polymer (from Example 26) | 0.03937 | 0.00342 |
| Low Heparin Combination Polymer (from Example 7) | −4.6E−18 | 0.001155 |
| High Heparin Combination Polymer (from Example 9) | 0.003856 | 0.00362 |

Example 32

Activity of Combination Polymer and Antimicrobial Polymer (Coated on Polyurethane Haemodialysis Catheters) Against *Enterococcus faecalis*

Catheters were coated as per the methodology set out in the relevant example (i.e. examples 21-27) and then tested for antimicrobial activity against *Enterococcus faecalis* as per example 28.

The turbidity results obtained are shown below in Table 3 and in FIG. 5.

TABLE 3

| Coating | Mean OD (600 nm) | SD |
| --- | --- | --- |
| Uncoated Dual Lumen 14Fr Polyurethane Dialysis Catheter | 0.472394 | 0.050788 |
| Antimicrobial Polymer (from Example 26) | 0.061583 | 0.065647 |
| Low Heparin Combination Polymer (from Example 7) | 0.062913 | 0.031085 |
| High Heparin Combination Polymer (from Example 9) | 0.03535 | 0.019943 |

Example 33

Activity of Combination Polymer and Antimicrobial Polymer Coated on Polyurethane Haemodialysis Catheters) Against *Escherichia coli* Post Plasma Incubation Catheters were coated as per the methodology set out in the relevant example (i.e. examples 21-27) and then tested for antimicrobial activity against *Escherichia coli* as per example 28. Prior to testing the sections were incubated in citrated human plasma overnight.

The turbidity results obtained are shown below in Table 4 and FIG. 6.

TABLE 4

| Coating | Mean OD (600 nm) | SD |
| --- | --- | --- |
| Uncoated Dual Lumen 14Fr Polyurethane Dialysis Catheter | 0.348924 | 0.0348 |
| Antimicrobial Polymer (from Example 26) | 0.117033 | 0.027831 |
| High Heparin Combination Polymer (from Example 9) | 0.000333 | 0.000957 |

Example 34

Activity of Combination Polymer and Antimicrobial Polymer (Coated on Polyurethane Haemodialysis Catheters) Against *Staphylococcus aureus* Post Plasma Incubation Catheters were coated as per the methodology set out in the relevant example (i.e. examples 21-27) and then tested for antimicrobial activity against *Staphylococcus aureus* as per example 28. Prior to testing the sections were incubated in citrated human plasma overnight.

The turbidity results obtained are shown below in Table 5 and FIG. 7.

TABLE 5

| Coating | Mean OD (600 nm) | SD |
| --- | --- | --- |
| Uncoated Dual Lumen 14Fr Polyurethane Dialysis Catheter | 0.213158 | 0.013578 |
| Antimicrobial Polymer (from Example 26) | 0.056938 | 0.009539 |
| High Heparin Combination Polymer (from Example 9) | 0.001063 | 0.001063 |

Example 35

Activity of Blended Polymer and Antimicrobial Polymer (Coated on Polyurethane Haemodialysis Catheters) Against *Staphylococcus aureus* Post Plasma Incubation Catheters were coated as per the methodology set out in the relevant example (i.e. examples 21-27) and then tested for antimicrobial activity against *Staphylococcus aureus* as per example 28. Prior to testing the sections were incubated in citrated human plasma overnight.

The turbidity results obtained are shown below in Table 6 and FIG. 8.

TABLE 6

| Coating | Mean OD (600 nm) | SD |
| --- | --- | --- |
| Uncoated | 0.82475 | 0.089052 |
| Antimicrobial Polymer from Example 26 | 0.0225 | 0.009883 |
| Blended Polymer (90:10) from Example 24 | 0.00675 | 0.005058 |
| Blended Polymer (75:25) from Example 25 | 0.00375 | 0.003862 |

Example 36

Activity of Blended Polymer and Antimicrobial Polymer (Coated on Polyurethane Haemodialysis Catheters) Against *Pseudomonas aeruginosa*

Catheters were coated as per the methodology set out in the relevant example (i.e. examples 21-27) and then tested for antimicrobial activity against *Pseudomonas aeruginosa* as per example 28.

The turbidity results obtained are shown below in Table 7 and FIG. 9.

TABLE 7

| Coating | Mean OD (600 nm) | SD |
| --- | --- | --- |
| Uncoated | 0.31 | 0.10924 |
| Antimicrobial Polymer from Example 26 | 0.114 | 0.017588 |
| Blended Polymer (90:10) from Example 24 | 0.028 | 0.032833 |
| Blended Polymer (75:25) from Example 25 | 0.07875 | 0.010046 |

Example 37

Platelet Adhesion to Uncoated, Blended Polymer, Antimicrobial and Combination Polymer Transparent samples were coated as per the methodology set out in the relevant example (i.e. examples 21-27). Platelet adhesion was then calculated by the methodology in Example 29.

The results obtained are below in Table 8 and FIGS. 10-12.

TABLE 8

| Coating | Mean Count | SD |
| --- | --- | --- |
| Uncoated Polystyrene | 401.0 | 28.1 |
| Uncoated Polyurethane | 551.7 | 70.1 |
| Combination Polymer (High Heparin) from Example 9 | 3.3 | 4.2 |
| Combination Polymer (Low Heparin) from Example 7 | 6.0 | 5.6 |
| Antimicrobial Polymer from Example 26 | 6.3 | 8.5 |
| Anticoagulant Polymer from Example 17 | 2.3 | 0.6 |
| Blended Polymer (90:10) from Example 24 | 3.0 | 3.6 |
| Blended Polymer (75:25) from Example 25 | 4.0 | 1 |

Example 38

Heparin Activity of Combination Polymer Over Time

Polyurethane sections were coated as per the methodology set out in the relevant example (i.e. examples 21-27). Pieces were then incubated in PBS at 37° C. and at set time points the heparin activity of pieces was measured using the methodology in example 30.

The results obtained are below in Table 9 and FIG. 13.

TABLE 9

| days in PBS | mU Hep/cm2 |
| --- | --- |
| 1 | 322.3 |
| 2 | 275.2 |
| 7 | 271.4 |
| 14 | 283.6 |
| 21 | 274.7 |
| 36 | 277.1 |
| 47 | 249.1 |
| 112 | 278.6 |

Example 39

Synthesis of polyhexamythlene guanide methacrylate (PHMG-MA)

30 g of Polyhexamethylene Guanidine Hydrochloride (PHMG, Chemos GmBH) in aqueous solution (~4 L of solution) was neutralised with a solution of 1.98 g of sodium hydroxide dissolved in 220 mL of water. Aqueous sodium hydroxide was slowly added (1 L/min) to the aqueous PHMG.

After the addition, the neutralised solution was frozen and ultimately freeze-dried to obtain a white powder of neutralised PHMG.

50 g of neutralised PHMG was dissolved in 125 mL of water. 1.86 mL of methacryloyl chloride was added to the solution and left to stir for a minimum of 1 hour, until the pH was 5.5 and the solution was totally clear.

The aqueous mixture was precipitated twice in tetrahydrofuran and washed twice in acetone. The precipitate was dried in a vacuum oven at 50° C. for 8-12 hours to obtain a white powder.

Example 40

Synthesis of Combination Polymer (Using PHMG-MA)

In a round-bottom flask, equipped with a condenser, a thermometer and a Pasteur pipette attachment to nitrogen inlet, 1 g of heparin poly(ethylene glycol) methacrylate (as per example 1) was dissolved in 28 mL of water. Subsequently, the following components were added into the flask: 13.5 g (solid) of methoxy poly(ethylene glycol) methacrylate of MW 2000, purified on charcoal and diluted at 20% (w/v), 2.98 g of methoxy poly(ethylene glycol) methacrylate of MW 350, 1 mL of methacrylic acid, 5.98 g of butyl methacrylate and 15 mL of isopropanol. The reflux condenser was turned on, the nitrogen allowed to bubble into the mixture of monomers and the heating turned up to warm up the mixture of monomers.

In a separate vial, 1.6 g of PHMG-MA (from example 39) was dissolved in 5 mL of water. In yet another vial, 150 mg of potassium persulfate was dissolved in 4 mL of water and degassed with nitrogen.

Once the mixture had reached a temperature of 70° C., the potassium persulfate aqueous solution was added to the mixture of monomers in the round bottom flask and the polymerisation started.

The PHMG-MA aqueous solution was then added. The polymerisation was allowed to progress for a total of 25-30 minutes and was quenched by adding 25 mL of icy cold water. The polymerisation solution was allowed to cool down to room temperature and was dialysed at a molecular weight cut off of 12-14 KDa against water overnight.

Example 41

Synthesis of an Antimicrobial Polymer

In a round-bottom flask, equipped with a condenser, a thermometer and a Pasteur pipette attachment to nitrogen inlet, 11.67 g of poly of PHMG-MA (from Example 39) was blended and dissolved in 140.7 mL of water. 81 g (solid) of methoxy poly(ethylene glycol) methacrylate of MW 2000, purified on charcoal and diluted at 20% (w/v), was added with 16.21 g of methoxy poly(ethylene glycol) methacrylate of MW 350, 11.22 mL of methacrylic acid, 37.33 g of butyl methacrylate and 84.8 mL of isopropanol. The reflux condenser was turned on, the nitrogen allowed to bubble into the mixture of monomers and the heating turned up to warm up the mixture of monomers.

In a separate vial, 905 mg of potassium persulfate was dissolved in 24 mL of water and degassed with nitrogen.

Once the mixture in the round bottom flask had reached a temperature of 70° C., the potassium persulfate aqueous solution was added to the mixture of monomers in the round bottom flask and the polymerisation started.

The polymerisation was allowed to progress to the desired level of viscosity and was quenched by the addition of 100 mL of icy cold water. Once cooled down to room temperature, the polymerisation solution was dialysed at a molecular weight cut off of 12-14 KDa against water overnight.

Example 42

Synthesis of an Antimicrobial Polymer

The polymer from example 39 in which methacrylic acid is replaced by 4-benzoylphenyl methacrylate (900 mg) during the synthesis, or in which both methacrylic acid and 4-benzoylphenyl methacrylate are jointly used.

Example 43

Synthesis of poly(ethylene glycol) methacrylate-PHMG)

4.8 g of sodium hydroxide was dissolved in 40 mL of water. The mixture was stirred and left to cool down to room temperature.

40 g of poly(ethylene glycol) methacrylate was added to the above mixture and left to stir for ~2 hours.

17.4 mL of epichlorohydrin was blended in a flask and the poly(ethylene glycol) methacrylate solution from above was blended in a dropping funnel and slowly added to the flask containing epichlorohydrin. The addition was completed over a period of ~2 hours 30 minutes.

The reaction mixture was then stirred at 45° C. for 16 hours.

After the 16 hour period, the water mixture was washed with diethyl ether via extraction. Then, the water layer was extracted with dichloromethane. The dichloromethane fraction was dried over a desiccant and the dichloromethane was evaporated using a rotary evaporator to yield a transparent oil of epoxy-poly(ethylene glycol) methacrylate.

57 g of neutralised PHMG (as per example 39) was dissolved in 240 mL of water. 10.8 g of the epoxy-poly (ethylene glycol) methacrylate was added to the neutralised poly(hexanide). The mixture was stirred at ~40° C. overnight (~16 hours).

After the 16 hour period, the mixture was precipitated twice in tetrahydrofuran and washed twice in acetone. The white paste was dissolved in a little amount of water, frozen and ultimately freeze-dried to obtain a white powder of poly(ethylene glycol) methacrylate PHMG.

Example 44

Synthesis of Combination Polymer (Using poly(ethylene glycol) methacrylate PHMG)

In a round-bottom flask, equipped with a condenser, a thermometer and a Pasteur pipette attachment to nitrogen inlet, 1 g of heparin poly(ethylene glycol) methacrylate (as per example 1) was dissolved in 28 mL of water. Subsequently, the following components were added into the flask: 13.5 g (solid) of methoxy poly(ethylene glycol) methacrylate of MW 2000, purified on charcoal and diluted at 20% (w/v), 2.98 g of methoxy poly(ethylene glycol) methacrylate of MW 350, 1 mL of methacrylic acid, 5.98 g of butyl methacrylate and 15 mL of isopropanol. The reflux condenser was turned on, the nitrogen allowed to bubble into the mixture of monomers and the heating turned up to warm up the mixture of monomers.

In a separate vial, 1.6 g of poly(ethylene glycol) methacrylate PHMG (from example 35) was dissolved in 5 mL of water. In yet another vial, 150 mg of potassium persulfate was dissolved in 4 mL of water and degassed with nitrogen.

Once the mixture had reached a temperature of 70° C., the potassium persulfate aqueous solution was added to the mixture of monomers in the round bottom flask and the polymerisation started.

The poly(ethylene glycol) methacrylate PHMG aqueous solution was then added. The polymerisation was allowed to progress for a total of 25-30 minutes and was quenched by adding 25 mL of icy cold water. The polymerisation solution was allowed to cool down to room temperature and was dialysed at a molecular weight cut off of 12-14 KDa against water overnight.

Example 45

Synthesis of an Antimicrobial Polymer

In a round-bottom flask, equipped with a condenser, a thermometer and a Pasteur pipette attachment to nitrogen inlet, 11.67 g of poly(ethylene glycol) methacrylate PHMG (from Example 43) was blended and dissolved in 140.7 mL of water. 81 g (solid) of methoxy poly(ethylene glycol) methacrylate of MW 2000, purified on charcoal and diluted at 20% (w/v), was added with 16.21 g of methoxy poly(ethylene glycol) methacrylate of MW 350, 11.22 mL of methacrylic acid, 37.33 g of butyl methacrylate and 84.8 mL of isopropanol. The reflux condenser was turned on, the nitrogen allowed to bubble into the mixture of monomers and the heating turned up to warm up the mixture of monomers.

In a separate vial, 905 mg of potassium persulfate was dissolved in 24 mL of water and degassed with nitrogen.

Once the mixture in the round bottom flask had reached a temperature of 70° C., the potassium persulfate aqueous solution was added to the mixture of monomers in the round bottom flask and the polymerisation started.

The polymerisation was allowed to progress to the desired level of viscosity and was quenched by the addition of 100 mL of icy cold water. Once cooled down to room temperature, the polymerisation solution was dialysed at a molecular weight cut off of 12-14 KDa against water overnight.

Example 46

Synthesis of an Antimicrobial Polymer

The polymer from example 39 in which methacrylic acid is replaced by 4-benzoylphenyl methacrylate (900 mg) during the synthesis, or in which both methacrylic acid and 4-benzoylphenyl methacrylate are jointly used.

The embodiments above are intended to be illustrative and not limiting. Additional embodiments are within the claims. In addition, although the invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

The invention claimed is:

1. A compound comprising
a random polymer of:
(i) a heparin-poly(ethylene glycol) methacrylate monomer having a single heparin,
(ii) methoxy(polyethylene glycol) methacrylate monomer,
(iii) butyl methacrylate monomer and/or methacrylic acid monomer and/or benzoylphenyl methacrylate monomer; and
(iv) poly(hexanide)-poly(ethylene glycol) methacrylate monomer and/or poly(hexanide) methacrylate monomer,
with the polymer being free of crosslinks.

2. The compound of claim 1 wherein the heparin is a heparin derivative, a heparin sulfate, a heparan sulfate, a heparin salt, or a heparin amine.

3. The compound of claim 1 wherein a ratio of a number of the heparin to a number of the hexanide groups on the polymer is between about 1:3 and about 1:25.

4. The compound of claim 3 wherein the ratio is between about 1:6 and about 1:20.

5. The compound of claim 1 wherein a concentration of the heparin compared to the polymer is between about 1% and about 20% w/w.

6. The compound of claim 5 wherein the concentration of the heparin compared to the polymer is between about 1.5% and about 8% w/w.

7. The compound of claim 1 wherein a concentration of the poly(hexanide) group compared to the compound is between about 2% and about 10% w/w.

8. The compound of claim 7 wherein the concentration of the poly(hexanide) group compared to the com pound is between about 6% and about 8% w/w.

9. The compound of claim 1 further comprising a lubricant group and/or an anti-fouling group covalently bound to the polymer.

10. The compound of claim 1 wherein a number of $CH_2CH_2O$ repeats in the heparin-poly(ethylene glycol) methacrylate monomer, methoxy(polyethylene glycol) methacrylate monomer, and the poly(hexanide)-poly(ethylene glycol) methacrylate monomer is independently selected to be from 1 to 50.

11. A polymeric coating comprising the compound of claim 1 blended with a lubricant and/or an anti-fouling compound.

12. The polymeric coating of claim 11 wherein the lubricant comprises an N-vinyl pyrrolidone group and/or a glycerol methacrylate group.

13. The polymeric coating of claim 11 wherein the anti-fouling compound is methacryloyloxyethyl phosphorylcholine, 2-((2-(methacryloyloxy)ethyl)dimethylammonio)ethyl 2-methoxyethyl phosphate, 2-((2-(methacryloyloxy)ethyl)dimethylammonio)propyl 2-methoxyethyl phosphate, or combinations thereof.

14. A medical device comprising a coating that comprises the compound of claim 1.

15. The medical device of claim 14 wherein the polymeric coating further comprises a lubricant agent and/or an anti-fouling functional agent.

16. The medical device of claim 15 wherein the lubricant agent is covalently bound to the polymer.

17. The medical device of claim 15 wherein the lubricant agent comprises an N-vinyl pyrrolidone group and/or a glycerol methacrylate group.

18. The medical device of claim 15 wherein the anti-fouling agent is covalently bound to the polymer.

19. The medical device of claim 15 wherein the antifouling agent is methacryloyloxyethyl phosphorylcholine, 2-((2-(methacryloyloxy)ethyl)dimethylammonio)ethyl 2-methoxyethyl phosphate, 2-((2-(methacryloyloxy)ethyl) dimethylammonio)propyl 2-methoxyethyl phosphate, or combinations thereof.

20. The medical device of claim 14 further comprising an artificial blood vessel, a cardiac stent, a venous stent, an arterial stent, a kidney stent, a ureter stent, a valve, a cardiac valve leaflet, a shunt, a cardiac device, a pacemaker, a transcutaneous catheter, a dialysis port, or a port for chemotherapy.

21. A method for making a polymer, the method comprising:
    polymerizing a mixture of:
    (i) heparin-poly(ethylene glycol) methacrylate monomer having a single heparin,
    (ii) methoxy(polyethylene glycol) methacrylate monomer,
    (iii) butylmethacrylate monomer and/or methacrylic acid monomer and/or benzovlphenyl methacrylate monomer; and
    (iv) poly(hexanide)-poly(ethylene glycol) methacrylate monomer and/or poly(hexanide) methacrylate monomer,
    with the polymer being made without crosslinks.

22. The method of claim 21 further comprising adding a free radical initiator to the mixture.

23. The method of claim 21 wherein the polymerizing step is performed between about 60° C. and about 80° C.

24. The method of claim 21 wherein the polymerizing step is terminated after no more than about 90 minutes.

25. The method of claim 21 wherein the polymerizing step is terminated after at least 20 minutes has passed.

26. The method of claim 21 wherein the ratio of a number of the heparin to a number of the hexanide groups on the polymer is between about 1:3 and about 1:25.

27. The method of claim 26 wherein the ratio is between about 1:6 and about 1:20.

* * * * *

UNITED STATES PATENT AND TRADEMARK OFFICE
CERTIFICATE OF CORRECTION

PATENT NO. : 10,206,945 B2
APPLICATION NO. : 14/263387
DATED : February 19, 2019
INVENTOR(S) : Simon Onis et al.

Page 1 of 1

It is certified that error appears in the above-identified patent and that said Letters Patent is hereby corrected as shown below:

In the Claims

Column 40, Claim 8, Line 33, please delete "com pound" and insert --compound--.

Signed and Sealed this
Fourteenth Day of May, 2019

Andrei Iancu
*Director of the United States Patent and Trademark Office*